United States Patent
Cheng et al.

(10) Patent No.: US 6,677,427 B1
(45) Date of Patent: *Jan. 13, 2004

(54) ENZYME-CATALYZED POLYAMIDES AND COMPOSITIONS AND PROCESSES OF PREPARING AND USING THE SAME

(75) Inventors: Huai N. Cheng, Wilmington, DE (US); Qu-Ming Gu, Hockessin, DE (US); William W. Maslanka, Landenberg, PA (US)

(73) Assignee: Hercules Incorporated, Wilmington, DE (US)

( * ) Notice: Subject to any disclaimer, the term of this patent is extended or adjusted under 35 U.S.C. 154(b) by 529 days.

This patent is subject to a terminal disclaimer.

(21) Appl. No.: 09/592,730

(22) Filed: Jun. 13, 2000

(51) Int. Cl.$^7$ .................. C08G 63/82; C08G 69/48; C08L 77/06; D21H 21/14; D21H 17/00

(52) U.S. Cl. .................. 528/310; 528/328; 528/170; 528/272; 528/274; 528/322; 528/341; 528/342; 525/7; 525/7.1; 525/8; 525/54.1; 525/430; 525/435; 524/606; 524/607; 524/608; 524/800; 524/845; 162/100; 162/111; 162/157.1; 162/157.3; 162/157.6; 162/164.3; 162/168.2; 162/184; 162/185

(58) Field of Search .................. 525/54.1, 7, 7.1, 525/8, 430, 435; 528/272, 170, 322, 274, 328, 341, 360, 361, 342; 524/606, 607, 608, 800, 845; 162/100, 111, 168.2, 157.1, 157.3, 157.6, 164.3, 184, 185

(56) References Cited

U.S. PATENT DOCUMENTS

| | | | |
|---|---|---|---|
| 2,926,116 A | | 2/1960 | Keim .................. 162/164 |
| 2,926,154 A | | 2/1960 | Keim .................. 260/29.2 |
| 4,388,439 A | * | 6/1983 | Maslanka .................. 524/845 |
| 4,501,640 A | | 2/1985 | Soerens |
| 4,908,150 A | | 3/1990 | Hessel et al. |
| 4,968,611 A | | 11/1990 | Traussnig et al. |
| 4,970,250 A | * | 11/1990 | Martinez et al. ............ 524/145 |
| 5,147,791 A | | 9/1992 | Morrow et al. |
| 5,338,807 A | * | 8/1994 | Espy et al. .................. 525/430 |
| 5,631,343 A | | 5/1997 | Binns et al. |
| 6,554,961 B1 | * | 4/2003 | Richle et al. ................ 528/487 |

FOREIGN PATENT DOCUMENTS

| | | | |
|---|---|---|---|
| EP | 320 121 | * | 6/1989 |
| EP | 0383405 | | 8/1990 |
| EP | 0425201 | | 5/1991 |
| EP | 0440165 | | 8/1991 |
| EP | 0 548 959 | | 6/1993 |
| WO | 94/12652 | | 6/1994 |
| WO | WO 98/32798 | | 7/1998 |
| WO | 99/61479 | | 12/1999 |
| WO | WO 00 39396 | | 7/2000 |

OTHER PUBLICATIONS

Gonsalves K.E. et al. "Synthesis and Properties of Degradable Polyamides and Related Polymers" Trends in Polymer Science, vol. 4, No. 1, Jan. 1996 pp. 25–31.

Jaeger K. E. et al. "Microbial Lipases Form Versitile Tools for Biotechnology" Trends in Biotechnology, vol. 16, No. 9, Sep. 1998, pp. 396–403.

H.H. Espy, "The Chemistry of Wet–Strength Broke Repulping", *Progress in Paper Recycling*, vol. 1, pp. 17–23 (1992), the month in the date of publication is not available.

Lock L. Chan, *Epoxidized Polyamide Wet Strength Resin* in Advanced Topics in Wet End Chemistry Seminar, pp. 1–18, (Atlanta, TAPPI Press 1985), the month in the date of publication is not available.

Djeghaba et al., "Enzymes in Organic Synthesis VII: Enzymatic Acylation of Amines", *Tetrahedron Letters*, vol. 32, pp. 761–762 (1991), the month in the date of publication is not available.

Wallace and Morrow, "Biocatalytic Synthesis of Polymers. Synthesis of an Optically Active, Epoxy–Substituted Polyester by . Lipase–Catalyzed Polymerization", *Journal of Polymer Science: Part A: Polymer Chemistry*, vol. 27, pp. 2553–2567 (1989), the month in the date of publication is not available.

Margolin et al., "Stereoselective Catalyzed by Lipases in Organic Solvents", *Tetrahedron Letters*, vol. 28, pp. 1607–1610 (1987), the month in the date of publication is not available.

Saotmoe et al., STN International, Chemical Abstracts, vol. 114, No. 13, p. 869 (1991), the month in the date of publication is not available.

Binns et al., STN International, Chemical Abstracts, vol. 119, No. 8, p. 73178 (1993), the month in the date of publication is not available.

Saotmoe et al., "Novel Enzymatically Degradable Polymers Comprising $\alpha$–Amino Acid, 1,2–Ethanediol and Adipic Acid", *Chemistry Letters*, vol. 1, pp. 21–24 (1991), the month in the date of publication is not available.

Binns et al., "Enzymic Polymerisation of an Unactivated Diol/Diacid System", *Journal of the Chemical Society Perkin Transactions*, vol. 1, pp. 899–904 (1993), the month in the date of publication is not available.

Dordick, "Enzymatic and Chemoenzymatic Approaches to Polymer Synthesis and Modification", *Annals of the New York Academy of Sciences*, vol. 672, pp. 352–362 (1992), the month in the date of publication is not available.

Kaplan et al., "Enzymes in Polymer Science: An Introduction", *ACS Symposium Series*, vol. 684, pp. 2–16 (1998), the month in the date of publication is not available.

(List continued on next page.)

Primary Examiner—P. Hampton-Hightower
(74) Attorney, Agent, or Firm—Joanna Rossi

(57) ABSTRACT

A polyamide, the enzymatic reaction product of at least one polyamine and diester, and processes for preparing and using the same. In addition, processes for preparing and using the enzymatic reaction product as creping adhesives and wet strength resins to make cellulose products.

158 Claims, No Drawings

OTHER PUBLICATIONS

Crescenzi and Dentini, "Microbes in Polymer Chemistry", *ACS Symposium Series,* vol. 627, pp. 221–232 (1996), the month in the date of publication is not available.

Rao et al., "Catalytic and Interfacial Aspects of Enzymatic Polymer Synthesis in Reversed Micellar Systems", *Biotechnology and Bioengineering,* vol. 41, pp. 531–540 (1993), the month in the date of publication is not available.

Shiro et al., Polymer Synthesis by Enzymatic Catalytic Polymerization, *Kagaku,* vol. 47, pp. 214–215 (1992).

Shiro et al., Enzymatic Catalyst for Synthesis of Natural and Unnatural Polymers, *Kagaku Kogyo,* vol. 44, pp. 567–571 (1993), the month in the date of publication is not available.

Noda et al., "Enzymatic Polymerization Catalyzed by Surfactant–Coated Lipases in Organic Media", *Biotechnology Letters,* vol. 19, pp. 307–309 (1997), the month in the date of publication is not available.

Chaudary et al., "Biocatalytic Solvent–free Polymerization to Produce High Molecular Weight Polyesters", *Biotechnology Progress,* vol. 13, pp. 318–325 (1997), the month in the date of publication is not available.

Gross, Enzymes in Polymer Synthesis: Whole Cell Biocatalysis, Abstract of Papers, Abstract No. 030, American Chemical Society, vol. 215 (1998), the month in the date of publication is not available.

Emmerling and Pfannemuller, Preparation of Oligosaccharide Aldonolactones and N–(2–Aminoethyl)aldonamides, *Carbohydrate Research,* vol. 86, pp. 321–324 (1980), the month in the date of publication is not available.

Kagan et al., "The Preparation of Glycamines", vol. 79, pp. 3541–3544 (1957). (Journal title unknown), the month in the date of publication is not available.

Ziegast and Pfannemuller, "Linear and Star–Shaped Hybrid Polymers, $2^{a)}$ Coupling of Mono– and Oligosaccharides to $\propto$, $\omega$–Diamino Substituted Poly(oxyethylene) and Multifunctional Amines by Amide Linkage", *Makromol. Chem. Rapid Commun.* vol. 5, pp. 373–379 (1984), the month in the date of publication is not available.

Kanerva et al., "Approach to Highly Enantiopure β–Amino Acid Esters by Using Lipase Catalysis in Organic Media", *Tetrahedron: Assymmetry,* vol. 7, pp. 1705–1716 (1996), the month in the date of publication is not available.

Vorde et al., "Resolution of 2–Methylalkanoic Esters: Enantioselective Aminolysis by (R)–1–Phenylethylamine of Ethyl 2–Methylocatanoate Catalysed by Lipase B from *Candida Antarctica*", *Tetrahedron: Assymmetry,* vol. 7, pp. 1507–1513 (1996), the month in the date of publication is not available.

Brazwell et al., "Biocatalytic Synthesis of Polymers. III. Formation of a High Molecular Weight Polyester through Limitation of Hydrolysis by Enzyme–Bound Water and Through Equilibrium Control", *Journal of Polymer Science Part A: Polymer Chemistry,* vol. 33, pp. 89–95 (1995), the month in the date of publication is not available.

Linko et al., "Lipase–Catalyzed Linear Aliphatic Synthesis in Organic Solvent", *Enzyme and Microbial Technology,* vol. 17, pp. 506–511 (1995), the month in the date of publication is not available.

Geresh and Gilboa, "Enzymatic Synthesis of Alkyd. II: Lipase–Catalyzed Polytransesterification of Dichloroethyl Fumarate with Aliphatic and Aromatic Diols", *Biotechnology and Bioengineering,* vol. 37, pp. 883–888 (1991), the month in the date of publication is not available.

Robert Schaffer and Horace S. Isbell, *Aldonic Acids* in Methods in Carbohydrate Chemistry, vol. II: Reactions of Carbohydrates, pp. 11–12, (Whistler RL, Wolfrom ML eds., New York, Academic Press, Inc. 1963), the month in the date of publication is not available.

* cited by examiner

ENZYME-CATALYZED POLYAMIDES AND COMPOSITIONS AND PROCESSES OF PREPARING AND USING THE SAME

BACKGROUND OF THE INVENTION

1. Field of the Invention

This invention relates to polyamides, and processes for making and using the same. In particular, the polyamide is an enzymatic reaction product of a polyamine and diester. The present invention is further directed to cellulose products as well as creping adhesives and wet strength resins comprising the enzymatic reaction product, and processes for preparing the same.

2. Background of the Invention and Related Information

Polyamides are extensively used in the papermaking industry as wet strength agents or creping aids in the production of tissue and towel paper products. The polyamides are usually synthesized via chemical processes using chemical catalysts at high temperatures and in the presence of organic solvents. Chemical processes provide an economical means for high production of polymers. However, the chemical catalysts lack the high selectivity required for the production of polymers having suitable properties such as high purity and appropriate molecular weight. Also, chemical production of polymers contributes to pollution throughout and after synthesis [Chaudhary et al., Biotechnol. Prog., 13, 318–325, (1997)].

Enzymes possess high selectivity and fast catalytic rates under mild conditions [Dordick, Ann. N.Y. Acad. Sci., 672, 352–362, (1992)]. The high selectivity reduces side reactions and allows easier separation and/or purification of the desired product. In addition, the ability to catalyze various types of organic reactions under mild conditions (e.g., ambient temperatures and pressure) makes the commercial use of enzymes highly feasible and attractive [Chaudhary et al., Biotechnol. Prog., 13, 318–325, (1997)]. Furthermore, the discovery that enzymes can function in reverse to catalyze esterifications and transesterifications, rather than the customary degradation or hydrolysis, has made enzymatic synthesis a competitive alternative to chemical synthesis of polymers [Dordick, Ann. N.Y. Acad. Sci., 672, 352–362, (1992); Brazwell et al., J. Polym. Sci. Part A: Polym. Chem., 33, 89–95, (1995)].

The enzymatic synthesis of small molecules has been extensively demonstrated using lipase [Djeghaba et al., Tetrahedron Lett., 32, 761–762, (1991); Kanerva et al., Tetrahedron Assymm., 7, 1705–1716, (1996); Vorde et al., Tetrahedron Assym., 7, 1507–1513, (1996)]. Larger molecules, such as polyesters have also been synthesized enzymatically, using lipase as the catalyst and in the absence or presence of organic solvents.

Chaudary et al. [Biotechnol. Prog., 13, 318–325, (1997)] disclose bulk polymerization of polyesters under ambient conditions with low concentrations of biocatalyst.

Brazwell et al. [J. Polym. Sci. Part A: Polym. Chem., 33, 89–95, (1995)] describe enzyme-catalyzed polycondensation with pig pancreas lipase to produce aliphatic polyesters.

Linko et al. [Enzyme Microb. Technol., 17, 506–511, (1995)] describe the enzymatic polymerization of bis(2,2,2-trifluoroethyl) sebacate and aliphatic diols in a transesterification reaction to produce linear polyesters.

Binns et al. [J. Chem. Soc. Perkin Trans., 1, 899–904, (1993)] describe the enzymatic synthesis of a low-dispersity polyester from the polyesterification of adipic acid and butane-1,4-diol by a commercial lipase.

Geresh et al. [Biotechnol. Bioeng., 37, 883–888, (1991)] describe the synthesis of unsaturated polyesters using lipases from different sources and in two different organic solvents, acetonitrile and tetrahydrofuran.

Additionally, WO 94/12652 discloses the enzymatic synthesis of polyesters or polyester(amide)s in the absence of solvent and presence of lipase.

Despite the numerous chemical methods for producing polyamides, there still remains a need in the art for preparing polyamides that will provide relatively pure, high molecular weight polyamides in high yields.

SUMMARY OF THE INVENTION

The present invention relates to polyamides, and processes for preparing and using the same. The polyamide of the present invention is the enzymatic reaction product of a polyamine and diester. The present invention has found that enzymatic synthesis of polyamides provides high yields of relatively pure polyamides with high molecular weight.

In particular, the present invention is advantageous in providing a highly selective enzymatic process for the synthesis of polyamides with high molecular weight under mild conditions and without the need for extraneous solvents. In addition, the enzyme may be optionally recycled for further use.

The present invention provides a process for preparing a polyamide which comprises reacting at least one diester and at least one polyamine in the presence of hydrolytic enzyme wherein the hydrolytic enzyme is at least about 0.01% by weight based on the total weight of the diester and polyamine, and the diester has the following general formula:

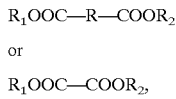

wherein R is a $C_1$ to $C_{20}$ hydrocarbyl group selected from one of alkyl, haloalkyl, alkylene, aryl, aralkyl, aralkylene, alkarylene, arylene, alkenyl or mixtures thereof; $R_1$ and $R_2$ are $C_1$ to $C_{22}$ hydrocarbyl group selected from alkyl, haloalkyl, alkylene, aryl, aralkyl, aralkylene, alkarylene, arylene, alkenyl or mixtures thereof; and wherein $R_1$ and $R_2$ may be the same or different; and the polyamine has the following general formula:

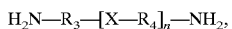

wherein $R_3$ and $R_4$ are $C_1$ to $C_6$ hydrocarbyl group selected from one of alkyl, haloalkyl, alkylene, aryl, aralkyl, aralkylene, alkarylene, arylene, alkenyl or mixtures thereof; X is selected from one or none of heteroatom or non-heteroatom, wherein the non-heteroatom comprises amine, thiol, carbonyl, carboxyl or $C_1$ to $C_6$ hydrocarbyl group selected from one of alkanol, alkyl, haloalkyl, alkylene, aryl, aralkyl, aralkylene, alkarylene, arylene or alkenyl; n is from 0 to 40; and wherein $R_3$ and $R_4$ may be the same or different.

In one embodiment of the invention, R is a $C_1$ to $C_4$ alkyl group, $R_1$ is a $C_1$ to $C_2$ alkyl group, $R_2$ is a $C_1$ to $C_2$ alkyl group, $R_3$ is a $C_2$ to $C_6$ alkyl group, $R_4$ is a $C_2$ to $C_6$ alkyl group, X is $CH_2$, O, S or NH, and n is 1 to 5.

In another embodiment of the invention, R is a $C_2$ to $C_4$ alkyl group, $R_1$ is a $C_1$ to $C_2$ alkyl group, $R_2$ is a $C_1$ to $C_2$ alkyl group, $R_3$ is a $C_2$ alkyl group, $R_4$ is a $C_2$ alkyl group, X is NH, and n is 1.

Additionally, the molecular weight of diesters of the present invention preferably range from about 100 to 1200 Daltons and most preferably from about 100 to 300 Daltons.

Suitable diesters of the present invention include dialkyl malonate, dialkyl fumarate, dialkyl maleate, dialkyl adipate, dialkyl glutarate, dialkyl succinate, dialkyl oxalate, dialkyl phenylmalonate or mixtures thereof.

The molecular weight of the polyamines of the present invention is preferably a range from about 40 to 10,000 Daltons and most preferably from about 40 to 2500 Daltons.

Suitable polyamines of the present invention include ethylenediamine (EDA), triethylene glycol diamine, bishexamethylenediamine (BHMT), hexamethylenediamine (HMDA), diethylenetriamine (DETA), triethylenetetramine (TETA), tetraethylenepentamine (TEPA), dipropylenetriamine (DPTA), tripropylenetetramine (TPTA), tetrapropylenepentamine (TPPA), N-methyl-bis-(aminopropyl)amine (MBAPA), spermine, spermidine, 1-phenyl-2,4-pentane diamine, 2-phenyl-1,3-propanediamine, phenylene diamine or mixtures thereof.

Enzymes of the present invention are obtained from natural (such as animals, plants, bacteria, yeast, fungi or virus) or synthetic sources (such as peptide synthesizer or expression vector). Natural sources include Candida species (such as *Candida antarctica*), Pseudomonas species (such as *Pseudomonas fluorescens* or Mucor species (such as *Mucor miehei*).

Suitable hydrolytic enzymes of the present invention are free or immobilized and include lipase, esterase or protease.

The hydrolytic enzyme is present in an amount preferably from about 0.01% to 10%, more preferably from about 0.1% to 5%, and most preferably from about 0.5% to 3% by weight based on the total weight of the diester and polyamine.

The hydrolytic enzyme of the present invention may be removed or denatured.

The molar ratio of the reactant ester group of the diester: reactant primary group of the amine group of the polyamine is preferably from about 0.8:2.0 to 2:0.8, and most preferably from about 0.95:1.1 to 1.1:0.95.

In one embodiment of the invention, the molar ratio of the reactant ester group of the diester:reactant primary group of the amine group of the polyamine is preferably from about 1:1.01 to 1:2, and most preferably from about 1:1.03 to 1:1.06.

The polyamide of the present invention may be present in aqueous solution at a final concentration of preferably greater than about 1% by weight and most preferably greater than about 40% by weight.

Polyamides of the present invention have a molecular weight polydispersity $(M_w/M_n)$ from about 1.2 to 5.0 and most preferably from about 2.2 to 3.0.

Accordingly, the polyamides of the present invention have a molecular weight range preferably from about 1,000 to 60,000 Daltons, and most preferably from about 4,000 to 12,000 Daltons.

Suitable polyamides of the present invention include water-soluble polyamides such as poly(diethylenetriamine adipamide), poly(diethylenetriamine glutaramide), poly(diethylenetriamine succinamide), poly(diethylenetriamine malonamide), poly(diethylenetriamine oxalamide), poly(diethylenetriamine fumaramide), poly(diethylenetriamine phenylmalonamide), poly(diethylenetriamine maleamide), poly(triethylenetetraamine adipamide), poly(triethylenetetraamine glutaramide), poly(triethylenetetraamine succinamide), poly(triethylenetetraamine malonamide), poly(triethylenetetraamine oxalamide), poly(tetraethylenepentaamine adipamide), poly(tetraethylenepentaamine glutaramide), poly(tetraethylenepentaamine succinamide), poly(tetraethylenepentaamine malonamide), poly(tetraethylenepentaamine oxalamide), poly(bis(hexamethylene)triamine adipamide), poly(bis(hexamethylene)triamine glutaramide), poly(bis(hexamethylene)triamine succinamide), poly(bis(hexamethylene)triamine malonamide), poly(bis(hexamethylene)triamine oxalamide), poly(triethyleneamine malonamide), poly(tetraethyleneamine malonamide) or mixtures thereof.

Suitable water-insoluble polyamides include poly(ethylene adipamide), poly(ethylene glutaramide), poly(ethylene succinamide), poly(ethylene malonamide), poly(ethylene oxalamide), poly(hexamethylene adipamide) or mixtures thereof.

In addition, the reaction temperature for preparing polyamides of the present invention is from about 24° C. to 130° C., and most preferably from about 50° C. to 100° C.

The process for preparing polyamides of the present invention may be substantially solvent-free or in the presence of at least one solvent. Such solvent includes methanol, ethylene glycol, glycerol, ethanol, t-butanol, isopropanol, water/NaCl, water/(NH$_4$Cl), water/(NH$_4$)$_3$SO$_4$, water/NH$_4$NO$_3$, water/(NH$_4$)PO$_4$ or mixtures thereof.

In a preferred embodiment of the invention, R is a $C_2$ to $C_4$ alkyl group, $R_1$ is a $C_1$ to $C_2$ alkyl group, $R_2$ is a $C_1$ to $C_2$ alkyl group, $R_3$ is a $C_2$ alkyl group, $R_4$ is a $C_2$ alkyl group, is NH, n is 1, the reaction temperature is from about 50° C. to 100° C. and the reaction is substantially in the absence of solvent.

In another preferred embodiment of the invention, R is —CH$_2$CH$_2$CH$_2$CH$_2$—, $R_1$ is CH$_3$, and $R_2$ is CH$_3$, wherein the polyamide is prepared in the presence of an immobilized hydrolytic enzyme derived from *Candida antarctica*, and the enzyme is present from about 0.5% to 3% by weight of enzyme based on the total weight of the diester and polyamine.

Another object of the present invention is to provide a polyamide which is the enzymatic reaction product of at least one polyamine and at least one diester, and having the general formula:

or

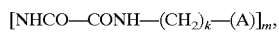

wherein when A is [X—(CH$_2$)$_k$]$_n$, X is selected from one or none of heteroatom or non-heteroatom, wherein the non-heteroatom comprises amine, thiol, carbonyl, carboxyl or $C_1$ to $C_6$ hydrocarbyl group selected from one of alkanol, alkyl, haloalkyl, alkylene, aryl, aralkyl, aralkylene, alkarylene, arylene or alkenyl; R is a $C_1$ to $C_{20}$ hydrocarbyl group selected from one of alkyl, haloalkyl, alkylene, aryl, aralkyl, aralkylene, alkarylene, arylene, alkenyl or mixtures thereof; n is 0 to 40; k is 1 to 6; and m is greater than or equal to 5;

wherein when A is

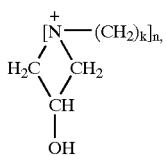

R is a $C_1$ to $C_{20}$ hydrocarbyl group selected from one of alkyl, haloalkyl, alkylene, aryl, aralkyl, aralkylene, alkarylene, arylene, alkenyl or mixtures thereof; n is 1 to 6; k is 1 to 6; and m is greater than or equal to 5; and wherein when A is

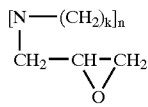

R is a $C_1$ to $C_{20}$ hydrocarbyl group selected from one of alkyl, haloalkyl, alkylene, aryl, aralkyl, aralkylene, alkarylene, arylene, alkenyl or mixtures thereof; n is 1 to 6; k is 1 to 6; and m is greater than or equal to 5.

In one embodiment of the invention, when the polyamide is

[NHCO—R—CONH—$(CH_2)_k$—(X—$(CH_2)_k)_n]_m$,

R is —$CH_2CH_2CH_2CH_2$—, X is O, n is 3, k is 2, and m is greater than 5; or R is $CH_2$—, X is NH, n is 1, k is 2, and m is greater than 5; or R is $CH(C_6H_5)$—, X is NH, n is 1, k is 2, and m is greater than 5; or R is CH=CH—, X is NH, n is 1, k is 2, and m is greater than 5.

In another embodiment of the invention, when the polyamide is

[NHCO—CONH—$(CH_2)_k$—(X—$(CH_2)_k)_n]_m$,

X is O, n is 3, k is 2, and m is greater than 5; or X is NH, n is 1, k is 2, and m is greater than 5.

Additionally, in one embodiment, the polyamide of the present invention is

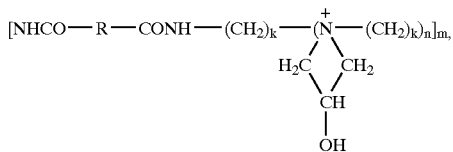

R is $CH_2$—, k is 2, n is 1, and m is greater than 5; or R is $CH(C_6H_5)$—, k is 2, n is 1, and m is greater than 5; or R is CH=CH—, k is 2, n is 1, and m is greater than 5; alternatively, when the polyamide is

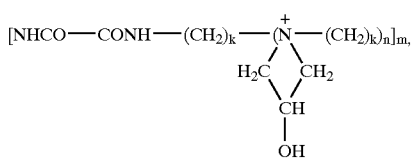

k is 2, n is 1, and m is greater than 5.

Further, in one embodiment of the invention, the polyamide is

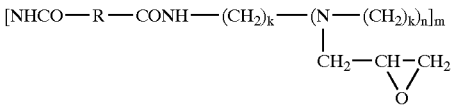

R is $CH_2$, k is 2, n is 1, and m is greater than 5; or R is $CHC_6H$, k is 2, n is 1, and m is greater than 5; or R is CH=CH, k is 2, n is 1, and m is greater than 5;

Even further, in one embodiment of the invention, the polyamide is

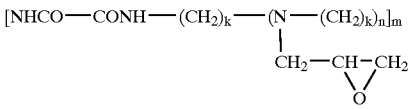

k is 2, n is 1, and m is greater than 5.

The polyamides of the present invention may have residues of at least one diester and at least one polyamine.

In addition, the final concentration of polyamides of the present invention in aqueous solution is preferably greater than about 1% by weight and most preferably greater than about 40% by weight.

In one embodiment of the invention, the polyamides may have a molecular weight polydispersity ($M_w/M_n$) range from about 2.2 to 3.0, molecular weight ($M_w$) range from about 4,000 to 12,000 Daltons, a molar ratio of the reactant ester group of the diester:reactant primary amine of the polyamine from about 0.95:1.1 to 1.1:0.95, and final concentration of polyamide in the aqueous solution is greater than about 40% by weight;

wherein the diester includes dimethyl malonate, dimethyl fumarate, dimethyl phenylmalonate or mixtures thereof; and wherein the polyamine includes triethylene glycol diamine, ethylenediamine (EDA), bis(hexamethylene triamine) (BHMT), hexamethylenediamine (HMDA), triethylenetetramine (TETA), tetraethylenepentamine (TEPA), dipropylenetriamine (DPTA), tripropylenetriamine (TPTA), tetrapropylenepentamine (TPPA), N-methyl-bis-(aminopropyl)amine (MBAPA), spermine, spermidine, 1-phenyl-2,4-pentane diamine, 2-phenyl-1,3-propanediamine, phenylenediamine or mixtures thereof.

The polyamides of the present invention may also include residues of ezye equal to or less than about 2% by weight of the polyamide.

Another object of the present invention is to provide a cellulose slurry comprising cellulose fibers and polyamides of the present invention. The cellulose slurry may also contain residues of enzyme.

Still another object of the present invention is to provide wet strength resins, creping adhesives and cellulose products comprising the polyamides, and processes for preparing and using the same.

A cellulose product of the present invention is prepared by adding at least one polyamide which is the enzymatic product of at least one diester and at least one polyamine, to a cellulose slurry.

The cellullose slurry may include at least one additive, the additive comprising at least one of cellulose fibers, fillers, coagulants, flocculants, wet strength or dry strength binders, retention aids, surfactants, sizing agents, chemical softeners, clay, titanium dioxide, metal silicates and calcium carbonate.

The cellulose product of the present invention may further comprise enzyme equal to or less than about 2% by weight of the polyamide.

The cellulose product may also include nonionic polymer from about 1% to 0.005% by weight based on paper.

Additionally, the cellulose product of the present invention may include polyamide-epihalohydrin resin from about 1% to 0.005% by weight based on paper.

The polyamide-epihalohydrin resin is a reaction product of at least one polyamide of the present invention and at least one epihalohydrin.

The molar ratio of epihalohydrin:secondary amine of the polyamide is preferably from about 0.02:1 to 2:1, and most preferably from about 0.5:1 to 1.5:1.

Polyamide-epihalohydrin resins of the present invention have a molecular weight range preferably from about 4,000 to 2,000,000 Daltons, and most preferably from about 10,000 to 100,000 Daltons.

Suitable epihalohydrins include epichlorohydrin, epibromohydrin or epiiodohydrin.

The reaction temperature for preparing polyamide-epihalohydrin resins of the present invention is from about 0° C. to 90° C.

The concentration of polyamide-epihalohydrin resin in aqueous solution is preferably from about 1% to 50%, and most preferably from about 10% to 15% by weight based on the total weight of the resin.

The Brookfield viscosity of the resin is preferably from about 1 to 1000 cps, and most preferably from about 10 to 200 cps.

The polyamide-epihalohydrin resin may include enzyme in an amount equal to or less than 2% by weight of the polyamide.

In a most preferred embodiment, the polyamide-epihalohydrin resin of the present invention has a molar ratio of epihalohydrin:secondary amine of the polyamide from about 0.5:1 to 1.5: 1, wherein the polyamide-epihalohydrin has a molecular weight range from about 10,000 to 100,000 Daltons; and the epihalohydrin is epichlorohydrin.

Furthermore, the polyamide-epihalohydrin resin may include at least one solvent selected from at least one of water/NaCl, water/$Na_2SO_4$, water/$NaNO_3$, water/$Na_3PO_4$, water/NH4Cl, water/$(NH_4)_3SO_4$, water/$NH_4NO_3$, water/$(NH_4)_3PO_4$ or mixtures thereof.

A strengthening aid composition is also provided in the present invention comprising polyamide-epihalohydrin resin and at least one solvent.

The strengthening aid is applied to a surface such as cellulose fiber web or drying surface, or slurry.

The strengthening aid of the present invention is applied to a slurry in an amount preferably from about 1 to 100 lb/ton, and most preferably from about 10 to 30 lb/ton.

Additionally, a creping composition is provided comprising polyamide-epihalohydrin resin and at least one nonionic polymer.

Suitable nonionic polymers include poly(vinyl alcohol), polyacrylamide, poly(ethylene oxide), poly(vinylpyrrolidinone) or mixtures thereof.

The creping adhesive is in a solids aqueous solution having a concentration preferably from about 35% to 10% solids, and most preferably from about 25% to 20% solids.

The fraction of polyamide-epihalohydrin resin in the solids aqueous solution is preferably from about 1% to 50%, and most preferably from about 5% to 25% by weight.

The fraction of nonionic polymer in the solids aqueous solution is preferably from about 90% to 10%, and most preferably from about 60% to 40% by weight.

The creping adhesive may be in an aqueous, solid, dispersion or aerosol form.

The adhesive may further include an enzyme present at an amount equal to or less than about 2% by weight of the polyamide.

The creping adhesive is used to crepe cellulose webs comprising sequentially or substantially simultaneously applying at least one polyamide-epihalohydrin resin and at least one nonionic polymer to a surface such as a drying surface.

Still another object of the present invention is to prepare a polyamide at a temperature to range from about 24° C. to 130° C.

DETAILED DESCRIPTION OF THE INVENTION

The present invention is directed to enzyme-catalyzed polyamides, and processes for producing polyamides by reacting at least one diester and at least one polyamine in the presence of a hydrolytic enzyme.

The process of the present invention is an enzymatic process that provides advantages over the existing chemical processes for industrial synthesis of polyamides. For example, the enzymatic process of the present invention may be carried out under milder conditions (e.g., ambient temperature) than the chemical processes, as known in the art. In addition, the process of the present invention produces an enzymatic reaction product with a narrower molecular weight distribution ($M_w/M_n$) than conventional chemical reaction products in the art. The enzyme can also be retrieved at the end of the process and optionally recycled, thus reducing production cost. Furthermore, the process of the present invention may occur in the presence or absence of solvents, whereas some chemical processes, as known in the art, require extraneous solvents which may reduce the pure yield and molecular weight of the polyamide. Preferably, the process of the present invention is carried out at low temperature and in the absence of solvents.

The enzymatic process of the present invention also provides polyamides with excellent purity that are otherwise poorly or cannot be produced by conventional chemical methods. Further, the enzymatic process of the present invention provides simple synthesis of high-molecular-weight polyamides, which are otherwise difficult to prepare using conventional chemica processes.

The polyamide of the present invention is the reaction product of at least one diester and at least one polyamine in the presence of a hydrolytic enzyme.

As used herein, the term "hydrocarbyl" refers to aliphatic, cycloaliphatic or aromatic. The hydrocarbyl groups are understood to include alkanol, alkyl, haloalkyl, alkylene, aryl, aralkyl, aralkylene, alkarylene, arylene or alkenyl groups. Further, hydrocarbyl is understood to include saturated or unsaturated, cyclic, branched or linear, non-substituted hydrocarbyl groups, and saturated or unsaturated, cyclic, branched or linear, substituted hydrocarbyl groups, with the latter referring to the hydrocarbon portion bearing additional substituents, besides carbon and hydrocarbon. Preferred hydrocarbyl groups include alkyl (such as methyl or ethyl) or haloalkyl (such as halomethyl or haloethyl) groups, and most preferred hydrocarbyl groups include alkyl groups.

The term "cellulosic fiber web" refers to sheets of paper made by a process which includes forming a papermaking furnish, depositing the furnish onto a foraminous surface, removing water from the web, and adhering the sheet to a drying surface such as a Yankee Dryer, and removing the sheet by a creping blade such as a doctor blade, as described in U.S. Pat. No. 4,501,640 to Soerens.

In addition, the term "cellulose product" refers to paper products including tissue paper or paper towels made from cellulosic fiber web as defined above.

Further, the term "heteroatom" refers to an atom other than carbon. Preferably, the heteroatom is N, S, or O. More preferably the heteroatom is S or O, and most preferably the heteroatom is N. Alternatively, "non-heteroatom" refers to atoms including amine, thiol, carbonyl, carboxyl, or $C_1$ to $C_6$ hydrocarbyl group selected from one of alkanol, alkyl, haloalkyl, alkylene, aryl, aralkyl, aralkylene, alkarylene, arylene or alkenyl. Preferably, the non-heteroatom is $CH_2$, NH or $N(CH_3)$. More preferably, the non-heteroatom is NH or $CH_2$, and most preferably the non-heteroatom is NH.

Furthermore, the term "substantially" refers to essentially, in essence, or to a large extent. "Substantially simultaneously applying" refers to adding two substances to a surface with substantially no time difference and essentially at the same position. The two substances being added can be in the form of a mixture as well as separately, e.g., by adding one substance during the addition of the other. The term "simultaneously" refers to occurring at the same time, and the term "individually" refers to singular or separate.

"Sequentially applying" refers to at least two different substances being individually added to different locations on a machine used to prepare cellulose products. These locations are far away enough so that the one substance added is mixed with the cellulose slurry before another substance is added.

Diesters suitable for use in the present invention include those with the general formula:

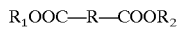

$R_1OOC-R-COOR_2$ or

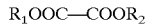

$R_1OOC-COOR_2$ wherein R is preferably a $C_1$ to $C_{20}$ hydrocarbyl group, more preferably R is a $C_1$ to C6 hydrocarbyl group, and most preferably, R is a $C_2$ to $C_4$ hydrocarbyl group. $R_1$ is preferably a $C_1$ to $C_{22}$ hydrocarbyl group, more preferably, $R_1$ is a $C_1$ to $C_6$ hydrocarbyl group, and most preferably $R_1$ is a $C_1$ to $C_2$ hydrocarbyl group. $R_2$ is preferably a $C_1$ to $C_{22}$ hydrocarbyl group, more preferably $R_2$ is a $C_1$ to $C_6$ hydrocarbyl group, and most preferably $R_2$ is a $C_1$ to $C_2$ hydrocarbyl group.

The diesters of the present invention have a molecular weight ($M_w$) range preferably from at least about 100 to 1200 Daltons, more preferably from at least about 100 to 600 Daltons, and most preferably from at least about 100 to 300 Daltons.

The diesters of the present invention include, but are not limited to, dialkyl malonate, dialkyl fumarate, dialkyl maleate, dialkyl adipate, dialkyl glutarate, dialkyl succinate, dialkyl oxalate, dialkyl phenylmalonate, or mixtures thereof.

Suitable polyamines include those with the following formula,

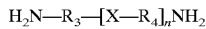

$H_2N-R_3-[X-R_4]_nNH_2$ where $R_3$ is preferably a $C_1$ to $C_6$ hydrocarbyl group, more preferably $R_3$ is a $C_2$ to $C_4$ hydrocarbyl group, and most preferably $R_3$ is a $C_2$ hydrocarbyl group. $R_4$ is preferably a $C_1$ to $C_6$ hydrocarbyl group, more preferably $R_4$ is a $C_2$ to $C_6$ hydrocarbyl group, and most preferably $R_4$ is a $C_2$ hydrocarbyl group. X is selected from one or none of heteroatom or non-heteroatom. Preferably X is O, $CH_2$, NH, $N(CH_3)$ or S, more preferably X is O, $CH_2$ or NH, and most preferably X is NH. "One or none of" refers to X being present as a heteroatom or non-heteroatom, or X may not be present in the formula. The number of the repeating unit is represented by n, ranging preferably from 0 to 40, more preferably n is 1 to 5, and most preferably n is 1.

In a more preferred embodiment, $R_3$ is a $C_2$ to $C_4$ hydrocarbyl group, n is 1 to 5, and X is $CH_2$, NH, or O. Most preferably, $R_3$ is a $C_2$ hydrocarbyl group, n is 1, and X is NH.

In another more preferred embodiment, $R_4$ is a $C_2$ to $C_4$ hydrocarbyl group, n is 1 to 5, and X is $CH_2$, NH, or O. Most preferably, $R_4$ is a $C_2$ hydrocarbyl group, n is 1, and X is NH.

The polyamines of the present invention have a molecular weight ($M_w$) range preferably from at least about 40 to 10,000 Daltons, more preferably from at least about 40 to 5,000 Daltons, and most preferably from at least about 40 to 2,500 Daltons.

The polyamines of the present invention include, but are not limited to, polyalkylpolyamine, polyalkylenepolyamine, polyaralkylenepolyamine, polyalkarylenepolyamine, polyarylenepolyamine or mixtures thereof.

The polyamines preferably include, but are not limited to, ethylenediamine (EDA), triethylene glycol diamine, bishexamethylenediamine (BHMT), hexamethylenediamine (HMDA), diethylenetriamine (DETA), triethylenetetramine (TETA), tetraethylenepentamine (TPPA), dipropylenetriamine (DPTA), tripropylenetetramine (TPTA), tetrapropylenepentamine (TPPA), N-methyl-bis-(aminopropyl)amine (MBAPA), spermine, spermidine, 1-phenyl-2,4-pentanediamine, 2-phenyl-1,3-propanediamine, phenylene diamine or mixtures thereof.

More preferably, the polyamines of the present invention include, but are not limited to, triethylene glycol diamine, diethylenetriamine (DETA), triethylenetetraamine (TETA), dipropylenetriamine (DPTA), tripropylenetetraamine (TPTA), tetrapropylenepentamine (TPPA), N-methyl-bis-(aminopropyl)amine (MBAPA) or mixtures thereof.

Most preferably, the polyamines of the present invention include, but are not limited to, diethylenetriamine (DETA), triethylenetetraamine (TETA) or mixtures thereof.

In a preferred embodiment of the invention, R is a $C_1$ to $C_4$ alkyl group, $R_1$ is a $C_1$ to $C_2$ alkyl group, $R_2$ is a $C_1$ to $C_2$ alkyl group, $R_3$ is a $C_2$ to $C_6$ alkyl group, R4 is a $C_2$ to $C_6$ alkyl group, X is $CH_2$, O, S or NH, and n is 1 to 5.

In another preferred embodiment of the invention, R is a $C_2$ to $C_4$ alkyl group, $R_1$ is a $C_1$ to $C_2$ alkyl group, $R_2$ is a $C_1$ to $C_2$ alkyl group, $R_3$ is a $C_2$ alkyl group, $R_4$ is a $C_2$ alkyl group, X is NH, and n is 1.

In still another preferred embodiment of the invention, R is a $C_2$ to $C_4$ alkyl group, $R_1$ is a $C_1$ to $C_2$ alkyl group, $R_2$ is a $C_1$ to $C_2$ alkyl group, $R_3$ is a $C_2$ alkyl group, $R_4$ is a $C_2$ alkyl group, X is NH, n is 1, the reaction temperature is from about 50° C. to 100° C. and the reaction is substantially in the absence of solvent.

Further, in another preferred embodiment of the invention, R is $-CH_2CH_2CH_2CH_2-$, $R_1$ is $CH_3$, and $R_2$ is $CH_3$, wherein the polyamide is prepared in the presence of an immobilized hydrolytic enzyme derived from *Candida antarctica*, and the enzyme is present from about 0.5% to 3% by weight of enzyme based on the total weight of the diester and polyamine.

The hydrolytic enzyme of the present invention can be any hydrolytic enzyme or mixture of enzymes derived from synthetic or natural sources. The term "hydrolytic" refers to cleavage of a bond, such as a peptide, ester or amide bond, by the addition of the elements of water, yielding two or more products. Synthetic sources of the hydrolytic-enzyme of the present invention include, but are not limited to, peptide synthesizer or expression vector. Natural sources of the hydrolytic enzyme of the present invention include, but are not limited to, animals, plants, bacteria, yeast, fungi or virus. Preferably, the enzyme is obtained from a natural source including, but are not limited to, Candida species such as *Candida antarctica*, Pseudomonas species such as *Pseudomonas fluorescence*, Mucor species such as *Mucor miehei* or Rhizomucor miehei. Most preferably, the enzyme is obtained from *Candida antarctica*.

The hydrolytic enzyme may be free or immobilized. The term "immobilized" refers to the enzyme being bound to an inert carrisuch as acrylic or polyurethane resin, or entrapped in an inert polymer such as Celite. Preferably, the hydrolytic enzyme is immobilized. The immobilized enzyme may be removed from the reaction mixture after completion of the polymerization and optionally reused in another reaction.

Furthermore, the hydrolytic enzyme may be fully or partially active. The hydrolytic enzyme of the present invention preferably includes, but is not limited to, lipase, esterase, protease or mixtures thereof. More preferably, the enzyme is lipase, protease or mixtures thereof. Most preferably, the enzyme is lipase. An example of lipase includes palatase. A Commercial example of lipase includes Novozym® 435 (available from Novo Nordisk).

The presence of enzyme is required in the process of the present invention. The amount of enzyme used in the present invention is preferably from about 0.01% to 10%, more preferably from about 0.1% to 5%, and most preferably from about 0.5% to 3% by weight based on the total weight of the diester and polyamine. The amount of enzyme used in the process of the present invention is critical. For instance, if less than 0.01% of enzyme is used, the polymeric reaction would be slowed down and result in a lower molecular weight product. If more than 10% of enzyme is used, the polymeric reaction would result in a much higher molecular weight product.

The enzyme used in the process of the present invention can be removed or denatured during or after completion of the reaction.

Polyamides of the present invention are prepared in a process involving polymerization of diester and polyamine reactants in the presence of enzyme-under mild conditions, and in the absence or presence of solvents. The reaction product is optionally dissolved in an aqueous solution, and the enzyme is optionally removed. The process of the present invention allows polymerization of reactants under mild conditions to provide high molecular weight ($M_w$) polyamides with a relatively narrow molecular weight distribution or molecular weight polydispersity ($M_w/M_n$).

The molar ratio of the reactant ester group of the diester to the reactant primary amine group of the polyamine may be approximately equal molar ratio. However, the reaction may be carried out with reactants in stoichiometric imbalance. The molar ratio of the reactant ester group of the diester: reactant primary amine group of the polyamine is preferably from about 0.8:2 to 2:0.8, more preferably from about 0.90:1.1 to 1.1:0.90, and most preferably from about 0.95:1.1 to 1.1:0.95.

In one embodiment of the invention, the molar ratio of reactants may be adjusted to produce a polyamide with terminal amine units. Such polyamides may be useful in the synthesis of other polymers. The molar ratio of the reactant ester group of the diester: reactant primary amine group of the polyamine is preferably from about 1:1.01 to 1:2, more preferably from about 1:1.02 to 1:1.5, and most preferably from about 1:1.03 to 1:1.06.

In a preferred embodiment, polyamides having high molecular weights and/or which cannot be made chemically, may be prepared by the enzymatic process of the present invention. Examples of preparation of such polyamides include the enzymatic reaction of malonic acid and diethylene triamine, fumaric acid and diethylene triamine, or maleic acid and diethylene triamine, to form a high-molecular-weight polymer.

The process of the present invention is preferably performed at a reaction temperature from about 24° C. to 130° C., more preferably from about 40° C. to 110° C., and most preferably from about 50° C. to 100° C.

If the polyamide is prepared using at least one solvent, the solvents and any byproduct molecules produced by the reaction may be removed during or after the reaction under normal or reduced atomspheric pressure, or by evaporating at from about 70° C. to 100° C.

As discussed, the process of the present invention may occur in the absence or presence of solvent. Examples of solvents preferably include, but are not limited to, methanol, ethylene glycol, glycerol ethanol, t-butanol, isopropranol, water/NaCl, water/$Na_2SO_4$, water/$NaNO_3$, water/$Na_3PO_4$, water/$NH_4Cl$, water/$(NH_4)_3SO_4$, water/$NH_4NO_3$ and water/$(NH_4)_3PO_4$. More preferably, the solvent includes methanol, ethanol, ethylene glycol, glycerol, water/NaCl and water/$Na_2SO_4$, and most preferably the solvent includes methanol, ethanol and ethylene glycol. For economic reasons, the process of the present invention is preferably performed in the absence of solvent.

Certain solvents such as ethylene glycol or glycerol can be added to the process of the present invention to prevent any solidification that may occur from about 50° C. to 80° C., as such solidification can slow down the polymerization reaction.

In a most preferred embodiment of the invention, R is a $C_2$ to $C_4$ alkyl group, $R_1$ is a $C_1$ to $C_2$ alkyl group, $R_2$ is a $C_1$ to $C_2$ alkyl group, $R_3$ is a $C_2$ alkyl group, $R_4$ is a $C_2$ alkyl group, X is NH, and n is 1, and the process has a reaction temperature from about 50° C. to 100° C., and occurs substantially in the absence of solvent.

In another most preferred embodiment, R is —$CH_2CH_2CH_2CH_2$—, $R_1$ is $CH_3$, and $R_2$ is $CH_3$, and the polyamide is prepared in the presence of a hydrolytic enzyme such as lipase derived from yeast *Candida antarctica*. The enzyme is immobilized, and present at an amount from about 0.5% to 3% by weight based on the total weight of the diester and polyamine.

The polyamides of the present invention may further comprise residues of the enzyme used in the reaction. In such a case, the amount of enzyme present is equal to or less than about 2%, more preferably equal to or less than about 1.5%, and most preferably equal to or less than about 1% by weight of the polyamide.

The polyamides of the present invention may also comprise residues of at least one diester and at least one polyamine from the reaction.

As discussed above, the present invention provides an enzymatic process for synthesizing polyamides from diester and polyamine monomers. The process allows synthesis of high molecular weight polyamides that are otherwise difficult to prepare using conventional chemical methods. Furthermore, the enzyme of the present invention may be recycled to reduce the cost of production. The polyamides prepared using the process of the present invention are high in molecular weight ($M_w$) as well as purity and yield. Although the polyamides may be linear or branched, the polyamides of the present invention are preferably linear and have a narrow molecular weight polydispersity ($M_w/M_n$). The polyamides of the present invention may also be water-soluble or water-insoluble. Preferably, the polyamides of the present invention are water-soluble.

The polyamide of the present invention include those having the following general formula:

or

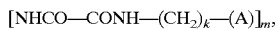

wherein when A is $[X-(CH_2)_k]_n$, X is selected from one or none of heteroatom or non-heteroatom; R is a $C_1$ to $C_{20}$ hydrocarbyl group; n is 0 to 40; k is 1 to 6; and m is greater than or equal to 5;
when A is

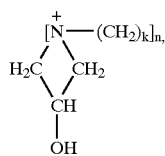

R is a $C_1$ to $C_{20}$ hydrocarbyl; n is 1 to 6; k is 1 to 6; and m is greater than or equal to 5; and
when A is

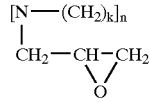

R is a $C_1$ to $C_{20}$ hydrocarbyl; n is 1 to 6; k is 1 to 6; and m is greater than or equal to 5.

In a preferred embodiment, the polyamide of the present invention has the formula:

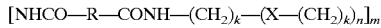

when R is $CH_2CH_2CH_2CH_2$—, X is O, n is 3, k is 2, and m is greater than 5; or when R is $CH_2$—, X is NH, n is 1, k is 2, and m is greater than 5; or when R is $CH(C_6H_5)$—, X is NH, n is 1, k is 2, and m is greater than 5; or when R is CH=CH—, X is NH, n is 1, k is 2, and m is greater than 5.

In another preferred embodiment, the polyamide of the present invention has the formula:

when X is O, n is 3, k is 2, and m is greater than 5; or when X is NH, n is 1, k is 2, and m is greater than 5.

In still another preferred embodiment, the polyamide of the present invention has the following formula:

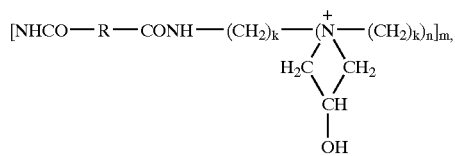

when R is $CH_2$—, k is 2, n is 1, and m is greater than 5; or when R is $CH(C_6H_5)$—, k is 2, n is 1, and m is greater than 5; or when R is CH=CH—, k is 2, n is 1, and m is greater than 5.

Further, in another preferred embodiment, the polyamide of the present invention has the formula:

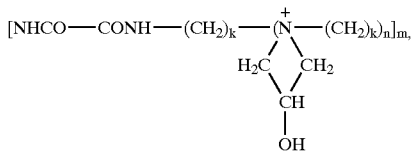

wherein k is 2, n is 1, and m is greater than 5.

Further, in still another preferred embodiment, the polyamide of the present invention has the following formula:

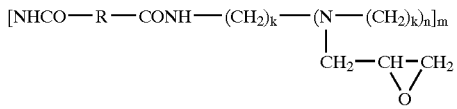

when R is $CH_2$, k is 2, n is 1, and m is greater than 5; or when R is $CHC_6H_5$, k is 2, n is 1, and m is greater than 5; or when R is CH=CH, k is 2, n is 1, and m is greater than 5.

Even further, in another preferred embodiment, the polyamide of the present invention has the following formula:

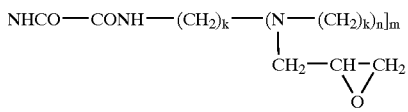

wherein k is 2, n is 1, and m is greater than 5.

Polyamides of the present invention includes water-soluble and water-insoluble polyamides.

The water-soluble polyamides of the present invention include Poly(diethylenetriamine adipamide), poly(diethylenetriamine glutaramide), poly(diethylenetriamine succinamide), poly(diethylenetriamine malonamide), poly(diethylenetriamine oxalamide), poly(diethylenetriamine fumaramide), poly(diethylenetriamine phenylmalonamide), poly(diethylenetriamine maleamide), poly(triethylenetetraamine adipamide), poly(triethylenetetraamine glutaramide), poly(triethylenetetraamine succinamide), poly(triethylenetetraamine malonamide), poly(triethylenetetraamine oxalamide), poly(tetraethylenepentaamine adipamide), poly(tetraethylenepentaamine glutaramide), poly(tetraethylenepentaamine succinamide), poly(tetraethylenepentaamine malonamide), poly(tetraethylenepentaamine oxalamide), poly(bis(hexamethylene)triamine adipamide), poly(bis(hexamethylene)triamine glutaramide), poly(bis(hexamethylene)triamine succinamide), poly(bis(hexamethylene)triamine malonamide), poly(bis(hexamethylene)triamine oxalamide), poly(triethyleneamine malonamide), poly(tetraethyleneamine malonamide) or mixtures thereof.

The water-insoluble polyamides of the present invention include poly(ethylene adipamide), poly(ethylene glutaramide), poly(ethylene succinamide), poly(ethylene malonamide), poly(ethylene oxalamide), poly(hexamethylene adipamide) or mixtures thereof.

The polyamides prepared by the process of the present invention are preferably dissolved in an aqueous solution. The final concentration of polyamides of the present invention in an aqueous solution is preferably greater than about 1% by weight, more preferably greater than about 10% by weight, and most preferably greater than about 40% by weight of the polyamide based on the total weight.

The polyamides of the present invention have a molecular weight polydispersity ($M_w/M_n$) range from about 1.2 to 5.0, preferably from about 2.0 to 4.0, and most preferably from about 2.2 to 3.0.

The polyamides of the present invention have a molecular weight ($M_w$) range preferably from about 1,000 to 60,000 Daltons, more preferably from about 2,000 to 20,000 Daltons, and most preferably from about 4,000 to 12,000 Daltons.

In one embodiment of the invention, the polyamides may have a molecular weight polydispersity ($M_w/M_n$) range from about 2.2 to 3.0, molecular weight ($M_w$) range from about 4,000 to 12,000 Daltons, a molar ratio of the reactant ester group of the diester:reactant primary amine of the polyamine from about 0.95:1.1 to 1.1:0.95, and final concentration of polyamide in the aqueous solution is greater than about 40% by weight; wherein the diester includes dimethyl malonate, dimethyl fumarate, dimethyl phenylmalonate or mixtures thereof; and wherein the polyamine includes triethylene glycol diamine, ethylenediamine (EDA), bis(hexamethylene triamine) (BHMT), hexamethylenediamine (HMDA), triethylenetetramine (TETA), tetraethylenepentamine (TEPA), dipropylenetriamine (DPTA), tripropylenetriamine (TPTA), tetrapropylenepentamine (TPPA), N-methyl-bis-(aminopropyl)amine (MBAPA), spermine, spermidine, 1-phenyl-2,4-pentane diamine, 2-phenyl-1,3-propanediamine, phenylenediamine or mixtures thereof.

Methods for determining the average molecular weight ($M_w$) of the polyamides of the present invention include, but are not limited to, size exclusion chromatography (SEC), solution viscosity or nuclear magnetic resonance (NMR).

In addition, analysis of the structure of polyamides of the present invention may be accomplished by any method known in the art. Preferably, such methods include, but are not limited to, infrared (IR) spectroscopy, proton nuclear magnetic resonance ($^1H$ NMR) spectroscopy, or carbon nuclear magnetic resonance ($^{13}C$ NMR) spectroscopy.

More preferably, such methods include, but are not limited to, SEC, IR, or $^1H$-NMR. Most preferably, such methods includes, but are not limited to, SEC, IR, or $^1H$-NMR.

Analysis of polyamides of the present invention by SEC, IR, $^1H$-NMR or $^{13}C$ NMR may be performed according to conventional methods known to one of skill in the art.

The polyamides of the present invention can be used in the process of papermaking. Specifically, the polyamides of the present invention can be used in a composition as a strengthening aid and/or a creping adhesive to prepare cellulos products.

The polyamides of the present invention may be reacted with epihalohydrin to form a polyamide-epihalohydrin resin that can be used in preparing cellulose products. The polyamide-epihalohydrin resin of the present invention can be used in the papermaking process for applications including strengthening aid and/or creping adhesive.

The polyarnide-epihalohydrin resin of the present invention includes thermosetting or non-thermosetting resins.

The polyamide-epihalohydrin resin of the present invention is prepared according to methods known in the art. The polyamide-epihalohydrin resin of the present invention is prepared in a one step process comprising reaction of at least one polyamide and at least one epihalohydrin in an aqueous medium. The reaction temperature range is preferably from about 0° C. to 90° C. More preferably, the temperature range is from about 50° C. to 70° C., and most preferably the temperature range is from about 55° C. to 65° C. The reaction is allowed to proceed until the desired molecular weight of the resin is achieved. The reaction is then optionally diluted and/or stabilized at an acidic pH with added acid.

The epihalohydrin of the present invention includes, but is not limited to, epichlorohydrin, epibromohydrin or epiiodohydrin. Preferably, the epihalohydrin is epichlorohydrin.

The molar ratio of epihalohydrin:secondary amine of the polyamide is preferably from about 0.02:1 to 2:1. More preferably, the molar ratio of epihalohydrin:secondary amine of the polyamide is from about 0.1:1 to 1.8:1. Most preferably, the molar ratio of epihalohydrin:secondary amine of the polyamide is from about 0.5:1 to 1.5:1.

The polyamide-epihalohydrin resin of the present invention has a molecular weight ($M_w$) range preferably from about 4,000 to 2,000,000 Daltons, more preferably from about 8,000 to 800,000 Daltons, and most preferably from about 10,000 to 100,000 Daltons.

The concentration of polyamide-epihalohydrin resin in an aqueous solution is preferably from about 1% to 50%, more preferably from about 5% to 25%, and most preferably from about 10% to 15% by weight based on the total weight of the resin.

In a most preferred embodiment, the polyamide-epihalohydrin resin of the present invention has a molar ratio of epihalohydrin:secondary amine of the polyamide from about 0.5:1 to 1.5:1, and wherein the polyamide-epihalohydrin has a molecular weight range from about 10,000 to 100,000 Daltons, and the epihalohydrin is epichlorohydrin.

The viscosity of the polyamide-epihalohydrin resin may be determined using methods known in the art such as the Gardner-Holdt method or Brookfield method. When using the Gardner-Holdt method, the sample is removed from the reaction vessel (e.g., approximately 15 g) and cooled to about 25° C. The sample is then transferred to a Gardner tube and brought up to the level of the first mark on the tube. The tube is then corked leaving an air space above the liquid. The sample tube is inverted and the rate of bubble rise in the sample tube is compared to the bubble rise in a set of Gardner-Holdt standards designated "A" (low viscosity) to "Z" (high viscosity). The standards are kept at 25° C. Once the desired Gardner-Holdt viscosity is reached, the resin can be diluted and the pH adjusted as necessary.

When the Brookfield method is used, the Brookfield viscosity is determined using a DV-I viscometer (Brookfield Viscosity Lab, Middleboro, Mass.). The process for determining the Brookfield viscosity includes attaching a spindle (number 2) to the viscometer which is set at a speed of 30 rotations per minute (rpm). A solution comprising 12.5% by weight of the polyamide composition is prepared. The spindle is then put into the solution and stirred at 30 rpm for 3 minutes at ambient temperature. The viscosity is then recorded in centipoises (cps). Preferably, the viscosity of the polyamide-epihalohydrin resin is determined using the Brookfield method.

The polyamide-epihalohydrin resin of the present invention has a Brookfield viscosity range preferably from about 1 to 1000 cps at 12.5% concentration in water. More preferably, the polyamide-epihalohydrin resin of the present invention has a Brookfield viscosity range from about 5 to 500 cps. Most preferably, the polyamide-epihalohydrin resin of the present invention has a Brookfield viscosity range from about 10 to 200 cps.

As discussed above, the polyamide-epihalohydrin resin of the present invention can be used as a strengthening aid to prepare cellulose products. Strengthening aids are generally used in papermaking to enhance the strength of the paper web. In particular, the polyamide-epihalohydrin resin of the present invention may be used as a strengthening aid to fortify cellulosic fiber webs in the process of papermaking.

The concentration of polyamide-epihalohydrin in an aqueous solution of strengthening aid is preferably from about 1% to 50% by weight, more preferably from about 5% to 25%, and most preferably from about 10% to 15% by weight.

The strengthening aid of the present invention may be a wet or dry strength agent. Further, the strengthening aid may be added directly or indirectly to the cellulosic fiber web.

The strengthening aid of the present invention may be applied onto the surface of the Yankee dryer (e.g., spraying), after which the cellulosic fiber web is pressed onto the dryer surface. In addition, the strengthening aid of the present invention may be applied onto the surface of the Yankee dryer alone or simultaneously with a creping adhesive formulation.

The strengthening aid of the present invention may also be added to a paper furnish or cellulosic slurry in an amount preferably from about 1 to 100 lb/ton, more preferably from about 5 to 50 lb/ton, and most preferably from about 10 to 30 lb/ton.

The use of the polyamide-epihalohydrin resin of the present invention as a strengthening aid to prepare cellulose products provides strong wet strength and dry strength properties, as well as fine paper qualities and excellent paper machine runnability.

Furthermore, the polyamide-epihalohydrin resin of the present invention can be used as a creping adhesive in preparing cellulose products. In particular, the creping adhesive can be used in a creping process to prepare cellulose products.

The creping process of the present invention can include the steps of applying the creping adhesive to a drying surface, preferably the surface of a Yankee Dryer, to provide a fibrous web, adhering the web to the drying surface by pressing the fibrous web against the surface, and creping the fibrous web with a creping device to dislodge it from the drying surface. Preferably, the creping device is a doctor blade.

The creping adhesive compositions of the present invention are obtained from the reaction of polyamide-epihalohydrin resin and nonionic polymer.

The nonionic polymer of the present invention includes, but is not limited to, poly(vinyl alcohol), polyacrylamide, poly(ethylene oxide), poly(vinylpyrrolidinone) or mixtures thereof. Preferably, the nonionic polymer is poly(vinyl alcohol).

As described herein, the term "solids" refers to the amount (in grams) of materials that are the active components or active ingredients of the present invention per gram of solution. The creping adhesives of the present invention are in an aqueous solution with solids content of polyamide-epihalohydrin and nonionic polymer.

The final concentration of solids in the aqueous solution is preferably from about 35% to 10% solids, more preferably from about 30% to 15% solids, and most preferably from about 25% to 20% solids.

The fraction of polyamide-epihalohydrin resin in the solids is preferably from about 1% to 50% by weight, more preferably from about 1% to 40% by weight, and most preferably from about 5% to 25% by weight.

The fraction of nonionic polymer in the solids is preferably from about 90% to 10% by weight, more preferably from about 75% to 25% by weight, and most preferably from about 60% to 40% by weight.

The application of creping adhesive of the present invention can be done in any manner known in the art, and in forms comprising aqueous, solid, dispersion or aerosol. Preferably, the creping adhesive is in the form of an aqueous solution or dispersion. The methods of application comprise simultaneous or sequential application of the polyamide-epihalohydrin and nonionic polymer to a drying surface or web to form the creping adhesive.

In addition, the creping adhesive can be added at the wet end of the paper machine or in the cellulose slurry. The cellulose slurry may comprise other additives such as cellulose fibers, fillers, coagulants, flocculants, wet strength or dry strength binders, retention aids, surfactants, sizing agents, chemical softeners, clay, titanium dioxide, metal silicates and calcium carbonate.

The creping adhesive compositions can also be used in conjunction with additives such as release agents, modifiers, surfactants, salts to adjust the water hardness, and/or acids or bases to adjust the pH of the creping adhesive composition, or other useful additives known in the art.

The use of the polyamide-epihalohydrin resin of the present invention as a creping adhesive to prepare cellulose products provides strong wet strength and dry strength properties, fine paper qualities and excellent paper machine runnability while increasing adhesion, dispersibility and uniform weting, as well as fine paper qualities and excellent paper machine runnability.

Further, when the polyamide-epihalohydrin resin of the present invention is used as a creping adhesive to prepare a cellulose product, the polyamide-epihalohydrin resin present in the cellulose product is preferably from about 1% to 0.005%, more preferably from about 0.5% to 0.05%, and most preferably from about 0.25% to 0.1% by weight based on paper.

The nonionic polymer present in the cellulose product is preferably from about 1% to about 0.005%, more preferably from about 0.5% to 0.05%, and most preferably from about 0.25% to 0. 1% by weight based on paper.

In addition, the strengthening aid of the present invention may be included with the creping adhesive formulation and then applied to the cellulosic fiber web.

When used as a strengthening aid, the polyamide-epihalohydrin resin present in the cellulose product is preferably from about 1% to 0.005%, more preferably from about 0.5% to 0.05%, and most preferably from about 0.25% to 0.1% by weight based on paper.

In the process for making cellulose products, certain additives such as retention aids, surfactants, sizing agents, softeners, fillers, coagulants, flocculants, clay, titanium dioxide, metal silicates or calcium carbonate or mixtures thereof, may be present in the cellulose product of the present invention. Other material can be present in the cellulose product so long as it does not interfere with or counteract the advantages of the creping adhesive and/or strengthening aid of the present invention.

Without further elaboration, it is believed that one skilled in the art can, using the preceding description, utilize the present invention to its fullest extent.

The following specific examples are, therefore, to be construed as merely illustrative, and not limitative of the remainder of the disclosure in any way whatsoever.

EXAMPLES

Example 1
SYNTHESIS OF POLYAMIDES

Polyamides of the present invention are prepared in a process involving oligomerization and polymerization of reactants in the presence of enzyme, under mild conditions and substantially no extraneous solvents. The polyamine and diester monomers are oligomerized and then reacted at a mild temperature, in the presence of enzyme, to allow polymerization of the oligomers. The reaction product is dissolved in an aqueous solution such as water or alkyl alcohol (e.g., methanol), and the enzyme is removed via filtration. This process allows polymerization of reactants under mild conditions to provide high molecular weight ($M_w$) reaction products with a relatively narrow molecular weight distribution. In addition, the reaction products are relatively pure due to the use of enzyme and substantial absence of solvents. Further still, the mild conditions prevent denaturation of the enzyme catalysts, and allow them to be optionally recycled for further use.

Example 2
ANALYSIS OF POLYAMIDES

Polyamides of the present invention are analyzed and prepared for analysis using methods known in the art.

$^{13}$C-NMR spectroscopy and $^1$H-NMR spectroscopy are performed using conventional methods known in the art. $^1$H-NMR spectroscopy is done using a Bruker AMX300 instrument with the spectral frequency at 300.1359 MHZ, sweep width at 6024 Hz, acquisition time of 2.72 seconds, additional pulse delay time of 1.00 seconds, number of scans at about 16, line broadening of 0.3 Hz, number of points at 32,000, pulse angle of 30°, and probe temperature of 298 Kelvin. $^3$C-NMR spectroscopy is also done with a Bruker AMX300 instrument but with the spectral frequency at 75.47549 MHZ, $^1$H decoupling (WALTZ) frequency at 300.1352 MHZ, sweep width at 25,000 Hz, aquisition time of 1.31 seconds, additional delay time of 2.00 seconds, line broadening of 1 Hz, number of scans at about 4000 Hz, number of points at 64,000 Kelvin, pulse angle of 30°, and probe temperature of 298 Kelvin.

Analysis of polyamides of the present invention via size exclusion chromatography is accomplished by the use of size exclusion columns (Eichrom CATSEC 4000, 1000, 300, 1.00 in series, 5–10 micrometer particle size) using Waters 515 series chromatographic equipment with a mixture of aqueous solution (1% sodium nitrate, 0.1 % trifluoroacetic acid) and acetonitrile (50:50, v/v) as the mobile phase. The detector is a Hewlett Packard 1047A differential refractometer. The molecular weight average is calculated using a Waters Millennium-32 data processing software from calibration against commercial standard poly(2-vinyl pyridine). Estimates of the number average (Mn) and weight average molecular weight (Mw) of the product mixtures are then computer-generated.

IR spectroscopy for analysis of polyamides of the present invention is accomplished using a Nicolet Magna 550 FT-IR spectrometer equipped with a MCT detector (which is cooled with liquid nitrogen), and a M-A-II type diamond anvil cell. A small portion of the sample is placed in a cell mounted on the beam condenser for examination. The spectrum is collected at a resolution of about 4cm$^{-1}$ through 250 co-added scans by 1 level of zero fill and Happ-Genzel anodization. A piece of silver chloride is then collected as a background to be calibrated against the samples.

Example 3

A. Samples No. 1–8 in Table 1 are prepared as described in Example 1. Small reaction bottles containing dimethyl adipate (0.348 g, 2 mmol) and diethylene triamine (0.216 g, 2.1 mmol) are mixed together at room temperature in the absence (No. 1) and presence of lipase (No. 2–8). Lipase (20 mg) is added to the appropriate bottle and the mixtures are incubated at room temperature. The samples are withdrawn after 24 hrs and 48 hrs incubations for analysis via infrared (IR) spectroscopy.

B. IR analysis of each sample is done as described in Example 2. The samples are withdrawn from incubation after 24 hrs and 48 hrs for analysis via IR spectroscopy. Completion of amidation is determined by the disappearance of the ester absorption peak (1745 cm–1) and the appearance of amide absorption peak (1650 cm–1).

Table I compares the extent of amidation in reaction samples (No. 1–8) of dimethyl adipate and diethylene triamine in the absence and presence of lipase.

Amidation in lipase-catalyzed samples (No. 2–8) is compared to a control sample without enzyme (No. 1). Control sample No. 1 shows low yield in comparison to the lipase-catalyzed samples (No. 2–8). Alternatively, lipase-catalyzed samples (No. 2–8) show higher product yield after 24 hrs and 48 hrs incubations. Even higher yield is observed with samples (No. 2, No. 3 and No. 6) which are catalyzed with lipase from Candida (available from Novo NorDisk), Pseudomonas (available from Sigma) and Mucor (available from Sigma) species of microorganisms after 24 hrs and 48 hrs. In particular, the highest yield is observed with sample No. 2, in which the lipase is derived from *Candida antarctica*.

TABLE I

Enzyme-Catalyzed Amidation between Dimethyl Adipate and Diethylene Triamine

| No. | Lipase sources | Appearance (24 hr) | Yield[4] (% at 24 hr) | Appearance (48 hr) | Yield[4] (% at 48 hr) |
|---|---|---|---|---|---|
| 1 | Control | Liquid | <2% | Liquid | 2–6% |
| 2 | *Candida antarctica*[1] | Solid | 30–40% | Solid | 60–70% |
| 3 | *Pseudomonas sp.*[2] | Liquid | 5–10% | Solid | 20–30% |
| 4 | *Candida rogasa*[3] | Liquid | — | Semi-solid | 10–15% |
| 5 | *Porcine panceas*[3] | Liquid | — | Liquid | — |
| 6 | *Mucor javanicus*[2] | Solid | 20–30% | Solid | 30–40% |
| 7 | *Penicillium camemberti*[2] | Liquid | — | Liquid | — |
| 8 | *Aspergillus niger*[2] | Liquid | — | Semi-solid | ~10% |

[1]From Novo Nordisk.
[2]From Sigma.

TABLE I-continued

Enzyme-Catalyzed Amidation between Dimethyl Adipate and Diethylene Triamine

| No. | Lipase sources | Appearance (24 hr) | Yield[4] (% at 24 hr) | Appearance (48 hr) | Yield[4] (% at 48 hr) |
|---|---|---|---|---|---|

[3]From Amano.
[4]Amide/[Amide + Ester], estimated by IR

Example 4

A. The samples in this example are prepared as described in Example 1. ethyl adipate (43.55 g, 0.25 mol), diethylene triamine (28.33 g, 0.275 mol) and Novozym (2.5 g) are mixed in a 250-ml flask. The reactants are then heated in an oil bath to 90° C. viscous mixture is stirred at 90° C. for 16 hrs in an open vessel with a stream of nitrogen. Completion of the reaction is indicated by the appearance of a yellowish solid. Methanol 150 ml) is then added to dissolve the polyamide product. The immobilized enzyme is insoluble in the methanol solution and is removed by filtration. Remaining methanol is removed by a rotary evaporator under low pressure. The final product is a yellowish solid with a yield of 48 g, $M_w$ of 8,400 Daltons, and $M_w/M_n$ of 2.73.

Under the same reaction conditions but in the absence of the enzyme, a polyamide also formed. The yield is 95% and the $M_w$ is determined by size exclusion chromatography to be 3,500 with a $M_w/M_n$ of 2.45. Analysis by size exclusion chromatography is performed as described in Example 2.

B. The chemical structure of the polyamide is characterized by IR spectroscopy, $^1$H NMR spectroscopy and $^{13}$C NMR spectroscopy, as described in Example 2. IR spectroscopy reveals formation of secondary amides by strong absorption peaks at 3300 cm$^{-1}$ (N-H stretch), 1650 cm$^{-1}$ (O=CNHR stretch band I) and 1560 cm$^{-1}$ (O=CNHR stretch band II). $^1$H NMR spectroscopy (in D$_2$O) shows four multiplets at 1.35–1.55 ppm for the central methylene in the adipic moiety, 2.05–2.20 ppm for the methylene adjacent to a carbonyl, 2.55–2.70 ppm for the methylene adjacent to the central amine of diethylene triamine, and 3.12–3.30 ppm for methylene adjacent to amide nitrogen. $^{13}$C NMR spectroscopy shows five peaks at 25.4 ppm for central carbons in the adipic moiety, at 35.8 ppm for carbons adjacent to carbonyl, at 39.1 ppm for carbons adjacent to the central amine of diethylene triamine, at 47.5 ppm for carbons adjacent to amide nitrogen, and at 177.0 ppm for amide carbons. The results confirm the structure of the polyamide.

Example 5

The following are further examples of preparation of polyamides of the present invention.

A. Dimethyl adipate (6.97 g, 0.04 mol), diethylene triamine (4.12 g, 0.04 mol) and Novozym 435 (0.5 g) are mixed in a 100 ml flask. The monomers are heated in an oil bath to 90° C. The viscous mixture is kept in the oil bath at 90° C. for 16 hrs in an open vessel with a stream of nitrogen. The reaction is complete with the appearance of a yellowish solid. Methanol (60 ml) is added to dissolve the polyamide product. The immobilized enzyme is insoluble in the methanol solution and is removed by filtration. Remaining methanol is removed by evaporation using a rotary evaporator under low pressure. The final product is a yellowish solid with a yield of 8.4 g, $M_w$ of 6,700 Daltons, and $M_w/M_n$ of 2.20.

B. Dimethyl malonate (39.40 g, 0.30 mol), diethylene triamine (30.90 g, 0.30 mol) and Novozym 435 (2 g) are mixed in a 250 ml flask. The reactants are heated in an oil bath at 80° C. The mixture is stirred at 80° C. for 16 hrs in an open vessel. After 1 hr, the reaction mixture is a light brown and a solid after 16 hrs. Methanol (150 ml) is added to dissolve the polyamide product. The immobilized enzyme is insoluble in the methanol solution and is removed by filtration. Remaining methanol is removed by a rotary evaporator under low pressure. The final product is a brown solid with a yield of 50 g, $M_w$ of 8,000 Daltons, and $M_w/M_n$ of 2.10.

C. Palatase, a lipase (from *Rhizomucor miehei* available from Novo Nordisk) is prepared into an immobilized Palatase powder. Analytical grade Celite (20 g) and 100 ml of 25% Palatase solution in 0.1M phosphate buffer at pH 7.0 are mixed and stirred at 10° C. for 3 hrs. The mixture is then lyophilized (freeze dried) to provide 37.6 g of immobilized Palatase powder.

Dimethyl malonate (26.40 g, 0.20 mol), diethylene triamine (20.60 g, 0.20 mol) and Celite-immobilized Palatase (2 g) are mixed in an open vessel. The reactants are heated in an oil bath to 70° C. The mixture is stirred at 70° C. for 16 hrs until the reaction mixture is a solid. Methanol (100 ml) is added to dissolve the polyamide product. The immobilized enzyme is insoluble in the methanol solution and is removed by filtration. Remaining methanol is removed by a rotary evaporator under low pressure. The final product is a brown solid with a yield of 27 g, $M_w$ of 15,790 Daltons, and $M_w/M_n$ of 1.83.

D. Diethyl phenylmalonate (23.6 g, 0.10 mol), diethylene triamine (10.3 g, 0.10 mol) and Novozym 435 (1 g) are mixed in a 500-ml flask. The reactants are heated in an oil bath to 100° C. The viscous mixture is stirred at 90° C.–100° C. for 24 hrs in an open vessel with a stream of nitrogen to a solid. The product is insoluble in most organic solvents and in water at neutral pH, but is soluble in water at pH 3. Water (150 ml) is added and the pH is adjusted to 3 by adding concentrated HCI. The immobilized enzyme is insoluble in water and is removed by filtration. The aqueous solution is lyophilized. The final product is a white solid with a yield of 26.9 g, $M_w$ of 3600 Daltons, and $M_w/M_n$ of 2.70.

E. Dimethyl adipate (17.42 g, 0.10 mol), triethylene glycol diamine (15.60 g, 0.105 mol) and Novozym® 435 (1.0 g) are mixed in a 250-ml open vessel. The reactants are heated in a stream of nitrogen in an oil bath to 70° C. for 24 hrs with stirring. The reaction mixture is then cooled and provides a viscous product. Methanol (100 ml) is added to dissolve the viscous product. The immobilized enzyme is insoluble in methanol and is removed by filtration. The remaining methanol in the reaction mixture is removed by a rotary evaporator under low pressure. The final product is a semi-solid with a yield of 28 g, $M_w$ of 4,540 Daltons, and $M_w/M_n$ of 2.71.

F. Dimethyl fumarate (14.4 g, 0.10 mol), diethylene triamine (10.3 g, 0.10 mol) and 1.0 g of Novozym 435 are mixed and stirred at 50° C. for 16 hrs under nitrogen. Methanol (50 ml) is then added to dissolve the product. The immobilized enzyme is insoluble in methanol and is removed by filtration. The remaining methanol is removed by evaporation using a rotary evaporator under low pressure. The final product is a sticky semi-solid with a yield of 23.0 g, $M_w$ of 3,060 Daltons, and $M_w/M_n$ of 1.85.

Example 6
Preparation of Polyamide-Epihalohydrin Resins

The polyamides in this example are prepared as described in Example 1.

The polyamide-epihalohydrin resins of the present invention are prepared according to methods known in the art. The resins are prepared in a one step process in which a polyamide and an epihalohydrin are reacted in an aqueous medium until the desired molecular weight is achieved. The reaction is then diluted and/or stabilized at an acidic pH with an added acid.

A. Poly(diethylenetriamine adipamide) (42.6 g, 0.20 mole) is added to a reaction vessel with 171 ml of water (pH 10.5). The solution is warmed to about 36° C.–37° C., and epichlorohydrin (23.3 g, 0.252 mole) is added. The reaction mixture is heated to 61 ° C.–64° C. and the viscosity is monitored until a Gardner-Holdt viscosity of J is achieved. Water (250 ml) is then added and the pH is adjusted to 4.4 with concentrated sulfuric acid. The reaction is diluted with water for a final product solids concentration of 12.5% solids, and Brookfield viscosity of 49 cps.

B. Poly(diethylenetriamine adipamide) (29.0 g, 0.169 mole) is added to a reaction vessel with 126 ml of water (pH 10.0). The solution is warmed to about 36° C. and epichlorohydrin (19.7 g, 0.213 mole) is added. The reaction mixture is heated to 70° C. and the viscosity is monitored until a Gardner-Holdt viscosity of J is achieved. Water (210 ml) is then added and the pH is adjusted to 4.5 with concentrated sulfuric acid. The final product is diluted with water for a final product solids concentration of 10.5% solids, and Brookfield viscosity of 55 cps.

Example 7
Evaluation of Tensile Strength

A. Resin A (diethylenetriamine adipamide-epihalohydrin resin) of the present invention is prepared via an enzymatic reaction as described in Example 6A. Kymene® 557H is prepared chemically and is commercially available from Hercules Incorporated.

The tensile strength of Resin A is compared to Kymene®557H. The resins are evaluated in handsheets prepared from a 50:50 softwood kraft/hardwood kraft blend which is beaten with 450 ml Canadian standard freeness at pH 7.5. The basic weight is 40 lbs/ream.

Table 2 shows the comparison between Resin A of the present invention and Kymene®557H. The tensile strength test shows comparable values between Kymene®557H (chemical synthesis) and Resin A (enzymatic synthesis) of the present invention. Similar dry and wet tensile strength values (lbs/in) are observed at the 0.25%, 0.50% and 0.75% levels of Resin A and Kymene®8557H. In particular, the wet tensile strength of both resins is increased after curing.

TABLE 2

| | | | Dry Tensile[a] | | Wet Tensile[a] | |
|---|---|---|---|---|---|---|
| | % Level | Basic Weight | Un-cured[b] | Cured[c] | Un-cured[b] | Cured[c] |
| Resin A | 0.25 | 40.0 | 16.2 | 15.1 | 2.70 | 3.02 |
| | 0.50 | 40.0 | 17.0 | 17.0 | 3.21 | 3.58 |
| | 0.75 | 40.0 | 16.8 | 17.0 | 3.39 | 3.78 |
| Kymene ® | 0.25 | 40.0 | 14.9 | 15.9 | 2.82 | 3.20 |

TABLE 2-continued

| | | | Dry Tensile[a] | | Wet Tensile[a] | |
|---|---|---|---|---|---|---|
| | % Level | Basic Weight | Un-cured[b] | Cured[c] | Un-cured[b] | Cured[c] |
| 557H | 0.50 | 40.0 | 16.9 | 16.8 | 3.49 | 3.79 |
| | 0.75 | 40.0 | 16.8 | 17.3 | 3.57 | 3.87 |

[a]lbs/in
[b]47 days natural aging
[c]80° C./30 min

B. Resin B (poly(diethylenetriamine adipamide-epichlorohydrin resin) of the present invention is prepared via an enzymatic reaction as described in Example 6B. Kymene®557H is prepared chemically and is commercially available from Hercules Incorporated.

The tensile strength of Resin B is compared to Kymene (557H. The resins are evaluated in handsheets prepared from a 50:50 softwood kraft/hardwood kraft blend beaten to 450 cc Canadian standard freeness at pH 7.5. The basic weight is 40 lbs/ream.

Table 3 shows the comparison between Resin B of the present invention and Kymene®557H. The tensile strength test shows comparable values between Kymene®557H (chemical synthesis) and Resin B (enzymatic synthesis) of the present invention. Similar dry and wet tensile strength values (lbs/in) are observed at the 0.50% level of Resin A and Kymene®557H. In particular, the wet tensile strength of both resins is increased after curing.

TABLE 3

| | | | Dry Tensile[a] | | Wet Tensile[a] | |
|---|---|---|---|---|---|---|
| | % Level | Basic Weight | Un-cured[b] | Cured[c] | Un-cured[b] | Cured[c] |
| Resin B | 0.50 | 40.0 | 16.4 | 17.6 | 3.07 | 3.40 |
| Kymene ® 557H | 0.50 | 40.0 | 14.5 | 16.7 | 3.15 | 3.48 |

[a]lbs/in
[b]9 days natural aging
[c]80° C./30 min

Example 8
Production of Cellulose Product

A 1% solids aqueous solution of creping adhesive is sprayed onto the surface of a Yankee Dryer along with the appropriate amount of release agent to provide a good balance of adhesion and release. This application optimizes both the productivity of the paper machine and the quality of the product produced on the machine. The solids consist of about 50% to 90% polyvinyl alcohol (PVOH) and about 10% to 50% polyamide-epihalohydrin resin. A cellulosic fibrous web is pressed against the drying surface to adhere the web to the surface. The dry web is then dislodged from the drying surface with a doctor blade and is wound on a reel. After the tissue material is converted to the final product (e.g., facial tissue, bath tissue, kitchen towel, etc.), it is then subjected to a sensory panel to obtain a softness rating.

Although the invention has been described with reference to particular means, materials and embodiments, it is to be understood that the invention is not limited to the particulars disclosed, and extends to all equivalents within the scope of the claims.

The preceding examples can be repeated with similar success by substituting the generically and specifically described constituents and/or operating conditions of this invention for those used in the preceding examples. From the foregoing descriptions, one skilled in the art can easily ascertain the essential characteristics of this invention, and without departing from the spirit and scope thereof, can make various changes and modifications of the invention to adapt to various usages and conditions.

What is claimed is:

1. A process for preparing a polyamide which comprises reacting (1) at least one diester, and (2) at least one polyamine in the presence of a hydrolytic enzyme, the diester has the following general formula:

$$R_1OOC-R-COOR_2$$

or $$R_1OOC-COOR_2$$

wherein R is a $C_1$ to $C_{20}$ hydrocarbyl group selected from one of alkyl, haloalkyl, alkylene, aryl, aralkyl, aralkylene, alkarylene, arylene, alkenyl or mixtures thereof; $R_1$ and $R_2$ are $C_1$ to $C_{22}$ hydrocarbyl group selected from alkyl, haloalkyl, alkylene, aryl, aralkyl, aralkylene, alkarylene, arylene, alkenyl or mixtures thereof; and wherein $R_1$ and $R_2$ may be the same or different;

the polyamine has the following general formula:

$$H_2N-R_3-[X-R_4]_n-NH_2$$

wherein $R_3$ and $R_4$ are $C_1$ to $C_6$ hydrocarbyl group selected from one of alkyl, haloalkyl, alkylene, aryl, aralkyl, aralkylene, alkarylene, arylene, alkenyl or mixtures thereof; X is selected from one or none of heteroatom or non-heteroatom, wherein the non-heteroatom comprises amine, thiol, carbonyl, carboxyl or $C_1$ to $C_6$ hydrocarbyl group selected from one of alkanol, alkyl, haloalkyl, alkylene, aryl, aralkyl, aralkylene, alkarylene, arylene or alkenyl; n is from 0 to 40; and wherein $R_3$ and $R_4$ may be the same or different; and the amount of hydrolytic enzyme present is at least about 0.01% by weight based on the total weight of the diester and polyamine.

2. The process of claim 1, wherein R is a $C_1$ to $C_4$ alkyl group; $R_1$ is a $C_1$ to $C_2$ alkyl group; $R_2$ is a $C_1$ to $C_2$ alkyl group; wherein $R_3$ is a $C_2$ to $C_6$ alkyl group; $R_4$ is a $C_2$ to $C_6$ alkyl group; wherein X is $CH_2$, O, S or NH; and n is 1 to 5.

3. The process of claim 2, wherein R is a $C_2$ to $C_4$ alkyl group; $R_1$ is a $C_1$ to $C_2$ alkyl group; $R_2$ is a $C_1$ to $C_2$ alkyl group; wherein $R_3$ is a $C_2$ alkyl group; $R_4$ is a $C_2$ alkyl group; wherein X is NH; and n is 1.

4. The process of claim 1, wherein the diester has a molecular weight range from at least about 100 to 1200 Daltons.

5. The process of claim 4, wherein the diester has a molecular weight range from at least about 100 to 300 Daltons.

6. The process of claim 4, wherein the diester comprises dialkyl malonate, dialkyl fumarate, dialkyl maleate, dialkyl adipate, dialkyl glutarate, dialkyl succinate, dialkyl oxalate, dialkyl phenylmalonate, or mixtures thereof.

7. The process of claim 6, wherein the polyamine has a molecular weight range from at least about 40 to 10,000 Daltons.

8. The process of claim 7, wherein the polyamine has a molecular weight range from at least about 40 to 2,500 Daltons.

9. The process of claim 7, wherein the polyamine comprises polyalkylpolyamine, polyalkenylpolyamine, polyaralkylenepolyamine, polyalkarylenepolyamine, polyarylenepolyamine or mixtures thereof.

10. The process of claim 9, wherein the polyamine comprises diethylene triamine (DETA), triethylene glycol diamine, ethylenediamine (EDA), bishexamethylenediamine (BHMT), hexamethylenediamine (HMDA), triethylenetetramine (TETA), tetraethylenepentamine (TEPA), dipropylenetriamine (DPTA), tripropylenetetramine (TPTA), tetrapropylenepentamine (TPPA), N-methyl-bis-(aminopropyl)amine (MBAPA), spermine, spermidine, 1-phenyl-2,4-pentane diamine, 2-phenyl-1,3-propanediamine, phenylene diamine or mixtures thereof.

11. The process of claim 9, wherein the hydrolytic enzyme is free or immobilized and comprises lipase, esterase or protease.

12. The process of claim 11, wherein the hydrolytic enzyme is from about 0.01% to 10% by weight based on the total weight of the diester and polyamine.

13. The process of claim 12, wherein the hydrolytic enzyme is from about 0.1% to 5% by weight based on the total weight of the diester and polyamine.

14. The process of claim 13, wherein the hydrolytic enzyme is from about 0.5% to 3% by weight based on the total weight of the diester and polyamine.

15. The process of claim 11, wherein the hydrolytic enzyme is obtained from a natural or synthetic source.

16. The process of claim 15, wherein the natural source comprises animals, plants, bacteria, yeast, fungi or virus.

17. The process of claim 16, wherein the natural source comprises Candida species, Pseudomonas species or Mucor species.

18. The process of claim 17, wherein the natural source comprises *Candida antarctica, Pseudomonas fluorescens* or *Mucor miehei.*

19. The process of claim 15, wherein the synthetic source comprises a peptide synthesizer or expression vector.

20. The process of claim 11, wherein the molar ratio of the reactant ester group of the diester:reactant primary amine group of the polyamine is from about 0.8:2.0 to 2.0:0.8.

21. The process of claim 20, wherein the molar ratio of the reactant ester group of the diester:reactant primary amine group of the polyamine is from about 0.95:1.1 to 1.1:0.95.

22. The process of claim 21, wherein the polyamide is in an aqueous solution.

23. The process of claim 22, wherein the final concentration of polyamide in the aqueous solution is greater than about 1% by weight.

24. The process of claim 23, wherein the final concentration of polyamide in the aqueous solution is greater than about 40% by weight.

25. The process of claim 20, wherein the polyamide has a molecular weight polydispersity ($M_w/M_n$) from about 1.2 to 5.0.

26. The process of claim 25, wherein the polyamide has a molecular weight polydispersity ($M_w/M_n$) from about 2.2 to 3.0.

27. The process of claim 25, wherein the polyamide has a molecular weight ($M_w$) range from about 1,000 to 60,000 Daltons.

28. The process of claim 27, wherein the polyamide has a molecular weight ($M_w$) range from about 4,000 to 12,000 Daltons.

29. The process of claim 27, wherein the polyamide is water-soluble or water-insoluble.

30. The process of claim 29, wherein the water-soluble polyamide comprises poly(diethylenetriamine adipamide), poly(diethylenetriamine glutaramide), poly (diethylenetriamine succinamide), poly(diethylenetriamine malonamide), poly(diethylenetriamine oxalamide), poly (diethylenetriamine fumaramide), poly(diethylenetriamine phenylmalonamide), poly(diethylenetriamine maleamide), poly(triethylenetetraamine adipamide), poly (triethylenetetraamine glutaramide), poly (triethylenetetraamine succinamide), poly (triethylenetetraamine malonamide), poly (triethylenetetraamine oxalamide), poly (tetraethylenepentaamine adipamide), poly (tetraethylenepentaamine glutaramide), poly (tetraethylenepentaamine succinamide), poly (tetraethylenepentaamine malonamide), poly (tetraethylenepentaamine oxalamide), poly(bis (hexamethylene)triamine adipamide), poly(bis (hexamethylene)triamine glutaramide), poly(bis (hexamethylene)triamine succinamide), poly(bis (hexamethylene)triamine malonamide), poly(bis (hexamethylene)triamine oxalamide), poly (triethyleneamine malonamide), poly(tetraethyleneamine malonamide) or mixtures thereof.

31. The process of claim 29, wherein the water-insoluble polyamide comprises poly(ethylene adipamide), poly (ethylene glutaramide), poly(ethylene succinamide), poly (ethylene malonamide), poly(ethylene oxalamide), poly (hexamethylene adipamide) or mixtures thereof.

32. The process of claim 27, wherein the reaction temperature for preparing the polyamide is from about 24° C. to 130° C.

33. The process of claim 32, wherein the reaction temperature for preparing the polyamide is from about 50° C. to 100° C.

34. The process of claim 32, comprising reacting substantially solvent-free.

35. The process of claim 32, comprising reacting in the presence of at least one solvent.

36. The process of claim 35, wherein at least one solvent comprises methanol, ethylene glycol, glycerol, ethanol, t-butanol, isopropanol, water/NaCl, water/$Na_2SO_4$, water/ $NaNO_3$, water/$Na_3PO_4$, water/$NH_4Cl$, water/$(NH_4)_3SO_4$, water/$NH_4NO_3$, water/$(NH_4)_3PO_4$ or mixtures thereof.

37. The process of claim 32, further comprises removing the hydrolytic enzyme.

38. The process of claim 32, further comprises denaturing the hydrolytic enzyme.

39. The process of claim 1, wherein R is a $C_2$ to $C_4$ alkyl group; $R_1$ is a $C_1$ to $C_2$ alkyl group; $R_2$ is a $C_1$ to $C_2$ alkyl group; wherein $R_3$ is a $C_2$ alkyl group; $R_4$ is a $C_2$ alkyl group; X is NH; and n is 1; and wherein the process has a reaction temperature from about 50° C. to 100° C., and substantially in the absence of solvent.

40. The process of claim 39, wherein R is —$CH_2CH_2CH_2CH_2$—, $R_1$ is $CH_3$, and $R_2$ is $CH_3$;

wherein the polyamide is prepared in the presence of a hydrolytic enzyme, the enzyme is a lipase derived from yeast *Candida antarctica;*
the enzyme is immobilized; and
the enzyme is from about 0.5% to 3% by weight of enzyme based on the total weight of the diester and polyarnine.

41. The process of claim 40, which further comprises removing the hydrolytic enzyme.

42. The process of claim 40, which further comprises denaturing the hydrolytic enzyme.

43. The process of claim 20, wherein the molar ratio of the reactant ester group of the diester:reactant primary amine group of the polyamine is from about 1:1.01 to 1:2.

44. The process of claim 43, wherein the molar ratio of the reactant ester group of the diester:reactant primary amine group of the polyamine from about 1:1.03 to 1:1.06.

45. A polyamide which is an enzymatic reaction product of at least one polyamine and at least one diester, the polyamide having the general formula:

or

wherein A is $[X—(CH_2)_k]_n$,
or

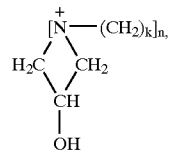 or 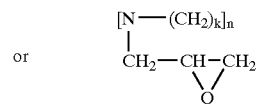

when A is $[X—(CH_2)_k]_n$, X is selected from one or none of heteroatom or non-heteroatom, wherein the non-heteroatom comprises amine, thiol, carbonyl, carboxyl or $C_1$ to $C_6$ hydrocarbyl group selected from one of alkanol, alkyl, haloalkyl, alkylene, aryl, aralkyl, aralkylene, alkarylene, arylene or alkenyl; R is a $C_1$ to $C_{20}$ hydrocarbyl group selected from one of alkyl, haloalkyl, alkylene, aryl, aralkyl, aralkylene, alkarylene, arylene, alkenyl or mixtures thereof; n is 0 to 40; k is 1 to 6; and m is greater than or equal to 5;

when A is

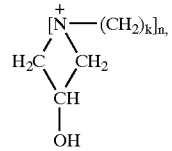

R is a $C_1$ to $C_{20}$ hydrocarbyl group selected from one of alkyl, haloalkyl, alkylene, aryl, aralkyl, aralkylene, alkarylene, arylene, alkenyl or mixtures thereof; n is 1 to 6; k is 1 to 6; and m is greater than or equal to 5; and when A is

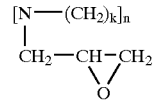

R is a $C_1$ to $C_{20}$ hydrocarbyl group selected from one of alkyl, haloalkyl, alkylene, aryl, aralkyl, aralkylene, alkarylene, arylene, alkenyl or mixtures thereof; n is 1 to 6; k is 1 to 6; and m is greater than or equal to 5.

46. The polyamide of claim 45, wherein the polyamide is

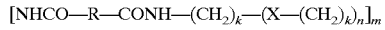

when R is $CH_2CH_2CH_2CH_2$—, X is O, n is 3, k is 2, and m is greater than 5; or when R is $CH_2$—, X is NH, n is 1, k is 2, and m is greater than 5; or when R is $CH(C_6H_5)$—, X is NH, n is 1, k is 2, and m is greater than 5; or when R is CH=CH—, X is NH, n is 1, k is 2, and m is greater than 5.

47. The polyamide of claim 45, wherein the polyamide is

[NHCO—CONH—(CH$_2$)$_k$—(X—(CH$_2$)$_k$)]$_m$ when X is O, n is 3, k is 2, and m is greater than 5; or
when X is NH, n is 1, k is 2, and m is greater than 5.

48. The polyamide of claim 45, wherein the polyamide is

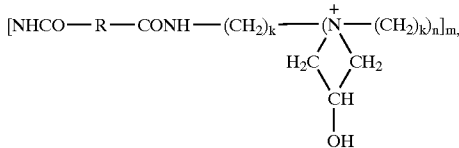

when R is CH$_2$—, k is 2, n is 1, and m is greater than 5; or
when R is CH(C$_6$H$_5$)—, k is 2, n is 1, and m is greater than 5; or
when R is CH=CH—, k is 2, n is 1, and m is greater than 5.

49. The polyamide of claim 45, wherein the polyamide is

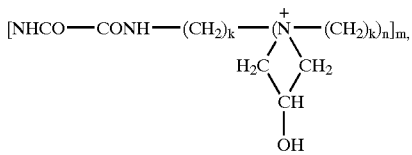

when k is 2, n is 1, and m is greater than 5.

50. The polyamide of claim 45, wherein the polyamide is

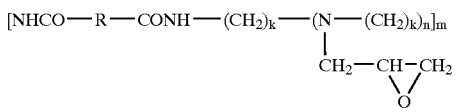

when R is CH$_2$, k is 2, n is 1, and m is greater than 5; or
when R is CHC$_6$H$_5$, k is 2, n is 1, and m is greater than 5; or
when R is CH=CH, k is 2, n is 1, and m is greater than 5.

51. The polyamide of claim 45, wherein the polyamide is

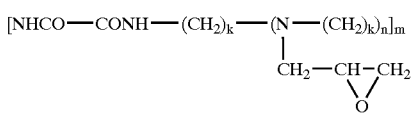

k is 2, n is 1, and m is greater than 5.

52. The polyamide of claim 45, wherein the polyamide comprises residues of at least one diester and at least one polyamine.

53. The polyamide of claim 52, wherein the diester has a molecular weight range from at least about 100 to 1200 Daltons.

54. The polyamide of claim 53, wherein the diester has a molecular weight range from at least about 100 to 300 Daltons.

55. The polyamide of claim 53, wherein the diester comprises dialkyl malonate, dialkyl fumarate, dialkyl maleate, dialkyl adipate, dialkyl glutarate, dialkyl succinate, dialkyl oxalate, dialkyl phenylmalonate or mixtures thereof.

56. The polyamide of claim 55, wherein the polyamine has a molecular weight range from at least about 40 to 10,000 Daltons.

57. The polyamide of claim 56, wherein the polyamine has a molecular weight range from at least about 40 to 2,500 Daltons.

58. The polyamide of claim 56, wherein the polyamine comprises polyalkylpolyamine, polyalkylenepolyamine, polyaralkylenepolyamine, polyalkarylenepolyamine, polyarylenepolyamine or mixtures thereof.

59. The polyamide of claim 58, wherein the polyamine comprises diethylene triamine, triethylene glycol diamine, ethylenediamine (EDA), bishexamethylenediamine (BHMT), hexamethylenediamine (HMDA), triethylenetetramine (TETA), tetraethylenepentamine (TEPA), dipropylenetriamine (DPTA), tripropylenetetramine (TPTA), tetrapropylenepentamine (TPPA), N-methyl-bis-(aminopropyl) amine (MBAPA), spermine, spermidine, 1-phenyl-2,4-pentane diamine, 2-phenyl-1,3-propanediamine, phenylene diamine or mixtures thereof.

60. The polyamide of claim 58, wherein the molar ratio of the reactant ester group of the diester:reactant primary amine group of the polyamine is from about 0.8:2.0 to 2.0:0.8.

61. The polyamide of claim 60, wherein the molar ratio of the reactant ester group of the diester:reactant primary amine group of the polyamine is from about 0.95:1.1 to 1.1:0.95.

62. The polyamide of claim 60, wherein the polyamide is in an aqueous solution.

63. The polyamide of claim 62, wherein the final concentration of polyamide in the aqueous solution is greater than about 1% by weight.

64. The polyamide of claim 63, wherein the final concentration of polyamide in the aqueous solution is greater than about 40% by weight.

65. The polyamide of claim 60, wherein the polyamide has a molecular weight polydispersity ($M_w/M_n$) from about 1.2 to 5.0.

66. The polyamide of claim 65, wherein the polyamide has a molecular weight polydispersity ($M_w/M_n$) from about 2.2 to 3.0.

67. The polyamide of claim 65, wherein the polyamide has a molecular weight ($M_w$) range from about 1,000 to 60,000 Daltons.

68. The polyamide of claim 67, wherein the polyamide has a molecular weight ($M_w$) range from about 4,000 to 12,000 Daltons.

69. The polyamide of claim 67, wherein the polyamide is water-soluble or water-insoluble.

70. The polyamide of claim 69, wherein the water-soluble polyamide comprises poly(diethylenetriamine adipamide), poly(diethylenetriamine glutaramide), poly(diethylenetriamine succinamide), poly(diethylenetriamine malonamide), poly(diethylenetriamine oxalamide), poly(diethylenetriamine fumaramide), poly(diethylenetriamine phenylmalonamide), poly(diethylenetriamine maleamide), poly(triethylenetetraamine adipamide), poly(triethylenetetraamine glutaramide), poly(triethylenetetraamine succinamide), poly(triethylenetetraamine malonamide), poly(triethylenetetraamine oxalamide), poly(tetraethylenepentaamine adipamide), poly(tetraethylenepentaamine glutaramide), poly(tetraethylenepentaamine succinamide), poly(tetraethylenepentaamine malonamide), poly(tetraethylenepentaamine oxalamide), poly(bis (hexamethylene)triamine adipamide), poly(bis(hexamethylene)triamine glutaramide), poly(bis(hexamethylene)triamine succinamide), poly(bis(hexamethylene)triamine malonamide), poly(bis(hexamethylene)triamine oxalamide), poly(triethyleneamine malonamide) or poly(tetraethyleneamine malonamide) or mixtures thereof.

71. The polyamide of claim 69, wherein the water-insoluble polyamide comprises poly(ethylene adipamide), poly(ethylene glutaramide), poly(ethylene succinamide), poly(ethylene malonamide), poly(ethylene oxalamide), poly(hexamethylene adipamide) or mixtures thereof.

72. The polyamide of claim 67, wherein the reaction temperature for preparing the polyamide is from about 24° C. to 130° C.

73. The polyamide of claim 72, wherein the reaction temperature for preparing the polyamide is from about 50° C. to 100° C.

74. The polyamide of claim 45, wherein the polyamide has the formula:

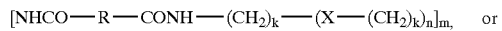

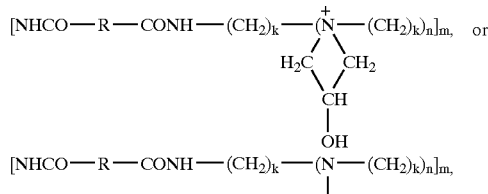

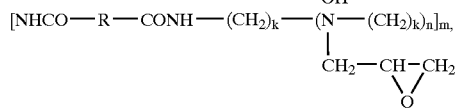

when the polyamide has the formula:

R is —CH$_2$CH$_2$CH$_2$CH$_2$—, —CH$_2$—, —CH(C$_6$H$_5$)— or —CH=CH—, wherein
    when R is —CH$_2$CH$_2$CH$_2$CH$_2$—, X is O, n is 3, k is 2, and m is greater than 5; or
    when R is —CH$_2$—, X is NH, n is 1, k is 2, and m is greater than 5; or
    when R is —CH(C$_6$H$_5$)—, X is NH, n is 1, k is 2, and m is greater than 5; or
    when R is —CH=CH—, X is NH, n is 1, k is 2, and m is greater than 5;

when the polyamide has the formula:

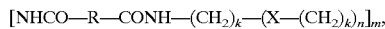

R is —CH$_2$—, —CH(C$_6$H$_5$)— or —CH=CH—, wherein
    when R is —CH$_2$—, k is 2, n is 1, and m is greater than 5; or
    when R is —CH(C$_6$H$_5$)—, k is 2, n is 1, and m is greater than 5; or
    when R is —CH=CH—, k is 2, n is 1, and m is greater than 5; and when the polyamide has the formula:

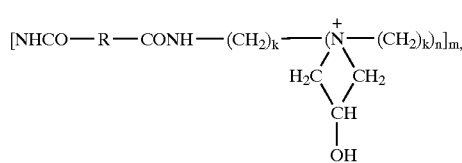

R is CH$_2$, CHC$_6$H$_5$ or CH=CH, wherein
    when R is CH$_2$, k is 2, n is 1, and m is greater than 5; or
    when R is CHC$_6$H$_5$, k is 2, n is 1, and m is greater than 5; or
    when R is CH=CH, k is 2, n is 1, and m is greater than 5.

75. The polyamide of claim 45, wherein the polyamide has the formula:

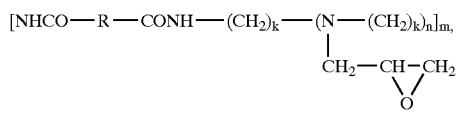

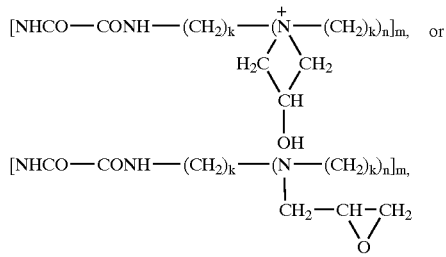

when the polyamide has the formula:

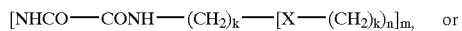

X is O or NH, wherein
    when X is O, n is 3, k is 2, and m is greater than 5; or
    when X is NH, n is 1, k is 2, and m is greater than 5; or when the polyamide has the formula:

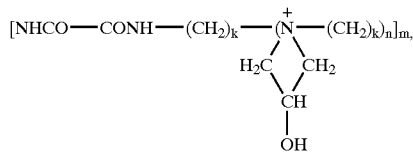

k is 2, n is 1, and m is greater than 5; or when the polyamide has the formula:

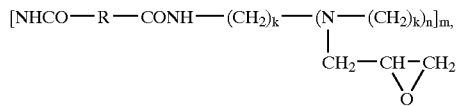

k is 2, n is 1, and m is greater than 5.

76. The polyamide of claim 74, wherein the polyamide has a molecular weight polydispersity from about 2.2 to 3.0, a molecular weight range from about 4,000 to 12,000 Daltons, a molar ratio of the reactant ester group of the diester:reactant primary amine of the polyamine from about 0.95:1.1 to 1.1:0.95, and final concentration of polyamide in the aqueous solution is greater than about 40% by weight;

wherein the diester comprises dimethyl malonate, dimethyl fumarate, dimethyl phenylmalonate or mixtures thereof; and wherein the polyamine comprises triethylene glycol diamine, ethylenediamine (EDA), bis(hexamethylene triamine) (BHMT), hexamethylenediamine (HMDA), triethylenetetramine (TETA), tetraethylenepentamine (TEPA), dipropylenetriamine (DPTA), tripropylenetriamine (TPTA), tetrapropylenepentaamine (TPPA), N-methyl-bis-(aminopropyl)amine (MBAPA), sperrnine, spermidine, 1-phenyl-2,4-pentane diamine, 2-phenyl-1,3-propanediamine, phenylenediamine or mixtures thereof.

77. The polyamide of claim 45, further comprising a hydrolytic enzyme.

78. The polyamide of claim 77, wherein the amount of hydrolytic enzyme present is equal to or less than about 2% by weight of the polyamide.

79. The polyamide of claim 74, wherein the polyamide further comprises a hydrolytic enzyme.

80. The polyamide of claim 79, wherein the amount of hydrolytic enzyme present is equal to or less than about 2% by weight of the polyamide.

81. The polyamide of claim 75, wherein the polyamide further comprises a hydrolytic enzyme.

82. The polyamide of claim 81, wherein the amount of hydrolytic enzyme present is equal to or less than about 2% by weight of the polyamide.

83. The polyamide of claim 60, wherein the molar ratio of the reactant ester group of the diester:reactant primary amine group of the polyamine is from about 1:1.01 to 1:2.

84. The polyamide of claim 83, wherein the molar ratio of the reactant ester group of the diester:reactant primary amine group of the polyamine from about 1:1.03 to 1:1.06.

85. A cellulose slurry comprising at least one polyamide, wherein the polyamide is the enzymatic reaction product of at least one polyamine and at least one diester, the polyamide having the general formula:

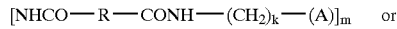

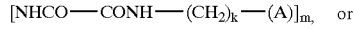

wherein A is [X—(CH₂)ₖ]ₙ,

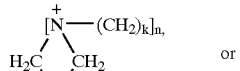

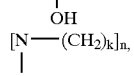

or

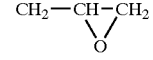

when A is [X—(CH₂)ₖ]ₙ, X is selected from one or none of heteroatom or non-heteroatom, wherein the non-heteroatom comprises amine, thiol, carbonyl or carboxyl, or $C_1$ to $C_6$ hydrocarbyl group selected from one of alkanol, alkyl, haloalkyl, alkylene, aryl, aralkyl, aralkylene, alkarylene, arylene or alkenyl; R is a $C_1$ to $C_{20}$ hydrocarbyl group selected from one or none of alkyl, haloalkyl, alkylene, aryl, aralkyl, aralkylene, alkarylene, arylene, alkenyl or mixtures thereof; n is 0 to 40; k is 1 to 6, and m is greater than or equal to 5; when A is

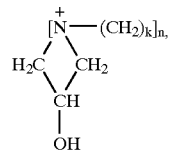

R is a $C_1$ to $C_{20}$ hydrocarbyl group selected from one or none of alkyl, haloalkyl, alkylene, aryl, aralkyl, aralkylene, alkarylene, arylene, alkenyl or mixtures thereof; k is 1 to 6; n is 1 to 6; and m is greater than or equal to 5; and
when A is

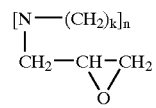

R is a $C_1$ to $C_{20}$ hydrocarbyl group selected from one or none of alkyl, haloalkyl, alkylene, aryl, aralkyl, aralkylene, alkarylene, arylene, alkenyl or mixtures thereof; k is 1 to 6; n is 1 to 6; and m is greater than or equal to 5.

86. The cellulose slurry of claim 85, wherein the polyamide has a molecular weight polydispersity from about 1.2 to 5.0.

87. The cellulose slurry of claim 86, wherein the polyamide has a molecular weight range of from about 1,000 to 60,000 Daltons.

88. The cellulose slurry of claim 87, wherein the polyamide is an enzymatic reaction product of at least one diester, at least one polyamine and at least one hydrolytic enzyme, wherein the diester comprises dialkyl malonate, dialkyl flumarate, dialkyl maleate, dialkyl oxalate, dialkyl phenylmalonate, dialkyl adipate, dialkyl succinate, dialkyl glutarate or mixtures thereof;

wherein the polyamine comprises diethylene triamine, triethylene glycol diamine, ethylenediamine (EDA), bishexamethylenediamine (BHMT), hexamethylenediamine (HMDA), triethylenetetramine (TETA), tetraethylenepentamine (TEPA), dipropylenetriamine (DPTA), tripropylenetetramine (TPTA), tetrapropylenepentamine (TPPA), N-methyl-bis-(aminopropyl)amine (MBAPA), spermine, spermidine, 1-phenyl-2,4-pentane diamine, 2-phenyl-1,3-propanediamine, phenylene diamine or mixtures thereof;

wherein the hydrolytic enzyme comprises lipase, esterase, protease or mixtures thereof; and wherein the slurry comprises one or none of cellulose fibers, fillers, coagulants, flocculants, clay, titanium dioxide, metal silicates or calcium carbonate.

89. The cellulose slurry of claim 88, further comprising a hydrolytic enzyme.

90. The cellulose slurry of claim 89, wherein the amount of hydrolytic enzyme present is equal to or less than about 2% by weight of the polyamide.

91. A process for preparing a cellulose product which comprises adding at least one polyamide to a cellulose slurry, wherein the polyamide is the enzymatic reaction product of at least one polyamine and at least one diester, the polyamide having the general formula:

[NHCO—R—CONH—(CH$_2$)$_k$—(A)]$_m$ or

[NHCO—CONH—(CH$_2$)$_k$—(A)]$_m$, wherein A is [X—(CH$_2$)$_k$]$_n$,

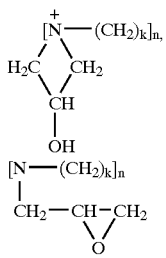

or when A is [X—(CH$_2$)$_k$]$_n$, X is selected from one or none of heteroatom or non-heteroatom, wherein the non-heteroatom comprises amine, thiol, carbonyl or carboxyl, or C$_1$ to C$_6$ hydrocarbyl group selected from one of alkanol, alkyl, haloalkyl, alkylene, aryl, aralkyl, aralkylene, alkarylene, arylene or alkenyl; R is a C$_1$ to C$_{20}$ hydrocarbyl group selected from one of alkyl, haloalkyl, alkylene, aryl, aralkyl, aralkylene, alkarylene, arylene, alkenyl or mixtures thereof; n is 0 to 40; k is 1 to 6, and m is greater than or equal to 5; when A is

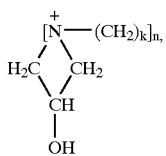

R is a C$_1$ to C$_{20}$ hydrocarbyl group selected from one of alkyl, haloalkyl, alkylene, aryl, aralkyl, aralkylene, alkarylene, arylene, alkenyl or mixtures thereof; k is 1 to 6; n is 1 to 6; and m is greater than or equal to 5; and when A is

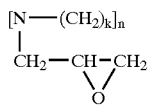

R is a C$_1$ to C$_{20}$ hydrocarbyl group selected from one alkyl, haloalkyl, alkylene, aryl, aralkyl, aralkylene, alkarylene, arylene, alkenyl or mixtures thereof; k is 1 to 6; n is 1 to 6; and m is greater than or equal to 5.

92. The process of claim 91, wherein the polyamide has a molecular weight polydispersity from about 1.2 to 5.0.

93. The process of claim 92, wherein the polyamide has a molecular weight range from about 1,000 to 60,000 Daltons.

94. The process of claim 93, wherein the cellulose slurry comprises at least one additive, the additive comprises at least one of cellulose fibers, fillers, coagulants, flocculants, wet strength or dry strength binders, retention aids, surfactants, sizing agents, chemical softeners, clay, titanium dioxide, metal silicates and calcium carbonate.

95. A cellulose product of claim 94.

96. The cellulose product of claim 95, further comprising a hydrolytic enzyme.

97. The cellulose product of claim 96, wherein the amount of hydrolytic enzyme present is equal to or less than about 2% by weight of the polyamide.

98. A cellulose product which comprises cellulose fibers and at least one residue of a polyamide,
wherein the polyamide is an enzymatic reaction product of at least one polyamine and at least one diester, the polyamide having the general formula:

[NHCO—R—CONH—(CH$_2$)$_k$—(A)]$_m$  or

[NHCO—CONH—(CH$_2$)$_k$—(A)]$_m$,  or wherein A is [X—(CH$_2$)$_k$]$_n$,

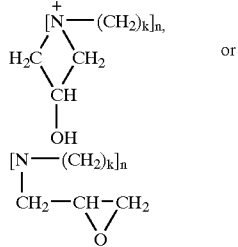

or when A is [X—(CH$_2$)$_k$]$_n$, X is selected from one or none of heteroatom or non-heteroatom, wherein the non-heteroatom comprises amine, thiol, carbonyl or carboxyl, or C$_1$ to C$_6$ hydrocarbyl group selected from one of alkanol, alkyl, haloalkyl, alkylene, aryl, aralkyl, aralkylene, alkarylene, arylene or alkenyl; R is a C$_1$ to C$_{20}$ hydrocarbyl group selected from one of alkyl, haloalkyl, alkylene, aryl, aralkyl, aralkylene, alkarylene, arylene, alkenyl or mixtures thereof: n is 0 to 40; k is 1 to 6, and m is greater than or equal to 5; when A is

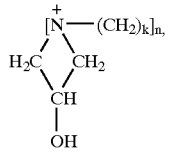

R is a C$_1$ to C$_{20}$ hydrocarbyl group selected from one of alkyl, haloalkyl, alkylene, aryl, aralkyl, aralkylene, alkarylene, arylene, alkenyl or mixtures thereof; k is 1 to 6; n is 1 to 6;
and m is greater than or equal to 5; and
when A is

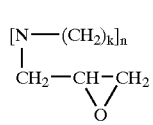

R is a C$_1$ to C$_{20}$ hydrocarbyl group selected from one of alkyl, haloalkyl, alkylene, aryl, aralkyl, aralkylene, alkarylene, arylene, alkenyl or mixtures thereof; k is 1 to 6; n is 1 to 6; and m is greater than or equal to 5.

99. The cellulose product of claim 98, wherein the polyamide has a molecular weight polydispersity from about 1.2 to 5.0.

100. The cellulose product of claim 99, wherein the polyamide has a molecular weight polydispersity from about 2.2 to 3.0.

101. The cellulose product of claim 99, wherein the polyamide has a molecular weight range from about 1,000 to 60,000 Daltons.

102. The cellulose product of claim 101, wherein the polyamide has a molecular weight range from about 4,000 to 12,000 Daltons.

103. The cellulose product of claim 97, further comprising polyamide-epihalohydrin resin.

104. The cellulose product of claim 103, wherein the polyamide-epihalohydrin resin is present from about 1% to 0.005% by weight based on paper.

105. The cellulose product of claim 98, further comprising nonionic polymer.

106. The cellulose product of claim 105, wherein the nonionic polymer is present from about 1% to 0.005% by weight based on paper.

107. A polyamide-epihalohydrin resin comprising at least one reaction product of at least one polyamide and at least one epihalohydrin, wherein the polyamide is the enzymatic reaction product of at least one polyamine and at least one diester, the polyamide having the general formula:

[NHCO—R—CONH—(CH$_2$)$_k$—(A)]$_m$ or

[NHCO—CONH—(CH$_2$)$_k$—(A)]$_m$, or wherein A is [X—(CH$_2$)$_k$]$_n$,

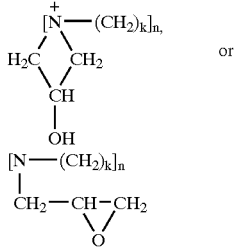

when A is [X—(CH$_2$)$_k$]$_n$, X is selected from one or none of heteroatom or non-heteroatom, wherein the non-heteroatom comprises amine, thiol, carbonyl or carboxyl, or C$_1$ to C$_6$ hydrocarbyl group selected from one of alkanol, alkyl, haloalkyl, alkylene, aryl, aralkyl, aralkylene, alkarylene, arylene or alkenyl; R is a C$_1$ to C$_{20}$ hydrocarbyl group selected from one of alkyl, haloalkyl, alkylene, aryl, aralkyl, aralkylene, alkarylene, arylene, alkenyl or mixtures thereof; n is 0 to 40; k is 1 to 6, and m is greater than or equal to 5;

when A is

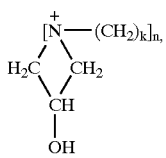

R is a C$_1$ to C$_{20}$ hydrocarbyl group selected from one of alkyl, haloalkyl, alkylene, aryl, aralkyl, aralkylene, alkarylene, arylene, alkenyl or mixtures thereof; k is 1 to 6; n is 1 to 6; and m is greater than or equal to 5; and when A is

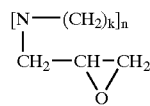

R is a C$_1$ to C$_{20}$ hydrocarbyl group selected from one of alkyl, haloalkyl, alkylene, aryl, aralkyl, aralkylene, alkarylene, arylene, alkenyl or mixtures thereof; k is 1 to 6; n is 1 to 6; and m is greater than or equal to 5.

108. The resin of claim 107, further comprising a hydrolytic enzyme.

109. The resin of claim 108, wherein the amount of hydrolytic enzyme present is equal to or less than 2% by weight of the polyamide.

110. The resin of claim 107, wherein the molar ratio of epihalohydrin:secondary amine of the polyamide is from about 0.02:1 to 2:1.

111. The resin of claim 110, wherein the molar ratio of epihalohydrin:secondary amine of the polyamide is from about 0.5:1 to 1.5:1.

112. The resin of claim 110, wherein the polyamide-epihalohydrin resin has a molecular weight range from about 4,000 to 2,000,000 Daltons.

113. The resin of claim 112, wherein the polyamide-epihalohydrin resin has a molecular weight range from about 10,000 to 100,000 Daltons.

114. The resin of claim 113, wherein the epihalohydrin comprises epichlorohydrin, epibromohydrin or epiiodohydrin.

115. The resin of claim 114, wherein the reaction temperature for preparing polyamide-epihalohydrin resin is from about 0° C. to 90° C.

116. The resin of claim 115, wherein the concentration of resin in an aqueous solution is from about 1% to 50% by weight based on the total weight of the resin.

117. The resin of claim 116, wherein the concentration of resin in an aqueous solution is from about 10% to 15% by weight based on the total weight of the resin.

118. The resin of claim 116, wherein the resin in an aqueous solution has a Brookfield viscosity from about 1 to 1000 cps.

119. The resin of claim 118, wherein the resin in an aqueous solution has a Brookfield viscosity from about 10 to 200 cps.

120. The resin of claim 110, wherein the molar ratio of epihalohydrin:secondary amine of the polyamide is from about 0.5:1 to 1.5:1;

wherein the polyamide has a molecular weight range from about 10,000 to 100,000 Daltons; and wherein the epihalohydrin comprises epichlorohydrin.

121. The resin of claim 120, wherein the composition further comprises at least one solvent selected from at least one of water/NaCl, water/Na$_2$SO$_4$, water/NaNO$_3$, water/Na$_3$PO$_4$, water/NH4Cl, water/(NH$_4$)$_3$SO$_4$, water/NH$_4$NO$_3$, water/(NH$_4$)$_3$PO$_4$ or mixtures thereof.

122. A strengthening aid composition which comprises the resin of claim 107, and at least one solvent.

123. The composition of claim 122, wherein the composition further comprises a hydrolytic enzyme.

124. The composition of claim 123, wherein the amount of hydrolytic enzyme present is equal to or less than 2% by weight of the polyamide.

125. The composition of claim 123, wherein the composition is in a form comprising aqueous, solid, dispersion or aerosol.

126. A process for preparing a cellulose product which comprises applying the strengthening aid of claim 125 to a surface or slurry.

127. The process of claim 126, wherein the surface comprises cellulose fiber web.

128. The process of claim 126, wherein the surface comprises a drying surface.

129. The process of claim 126, wherein the strengthening aid is applied to a slurry in an amount from about 1 to 100 lb/ton.

130. The process of claim 129, wherein the strengthening aid is applied to a slurry in an amount from about 10 to 30 lb/ton.

131. A composition comprising the resin of claim 107, and at least one nonionic polymer.

132. The composition of claim 131, wherein the nonionic polymer comprises poly(vinyl alcohol), polyacrylamide, poly(ethylene oxide), poly(vinylpyrrolidinone) or mixtures thereof.

133. A creping adhesive comprising the composition of claim 131.

134. The creping adhesive of claim 133, wherein the creping adhesive is in a solids aqueous solution.

135. The creping adhesive of claim 134, wherein the concentration of solids in the solids aqueous solution is from about 35% to 10% solids.

136. The creping adhesive of claim 135, wherein the concentration of solids in the solids aqueous solution is from about 25% to 20% solids.

137. The creping adhesive of claim 135, wherein the fraction of polyamide-epihalohydrin resin in the solids aqueous solution is from about 1% to 50% by weight.

138. The creping adhesive of claim 137, wherein the fraction of polyamide-epihalohydrin resin in the solids aqueous solution is from about 5% to 25% by weight.

139. The creping adhesive of claim 137, wherein the fraction of nonionic polymer in the solids aqueous solution is from about 90% to 10% by weight.

140. The creping adhesive of claim 139, wherein the fraction of nonionic polymer in the solids aqueous solution is from about 60% to 40% by weight.

141. The creping adhesive of claim 139, wherein the resin in an aqueous solution has a Brookfield viscosity from about 1 to 1000 cps.

142. The creping adhesive of claim 141, wherein the resin in an aqueous solution has a Brookfield viscosity from about 10 to 200 cps.

143. The creping adhesive of claim 133, wherein the creping adhesive is in a form comprising aqueous, solid, dispersion or aerosol.

144. The creping adhesive of claim 143, further comprising a hydrolytic enzyme.

145. The creping adhesive of claim 144, wherein the amount of hydrolytic enzyme present is equal to or less than about 2% by weight of the polyamide.

146. A process for creping cellulose webs which comprises the step of applying (1) at least one polyamide-epihalohydrin resin of claim 107, and (2) at least one nonionic polymer to a surface.

147. The process of claim 146, wherein the applying step comprises substantially simultaneously applying polyamide-epihalohydrin resin and nonionic polymer to a surface.

148. The process of claim 146, wherein the applying step comprises sequentially applying polyamide-epihalohydrin resin and nonionic polymer to a surface.

149. The process of claim 146, wherein the nonionic polymer comprises poly(vinyl alcohol), polyacrylamide, poly(ethylene oxide), poly(vinylpyrrolidinone) or mixtures thereof.

150. The process of claim 149, wherein the surface is a drying surface.

151. A process for preparing a polyamide which comprises reacting (1) at least one diester and (2) at least one polyamine at temperature from about 24° C. to 130° C., the diester has the following general formula:

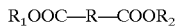

or

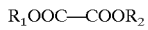

wherein R is a $C_1$ to $C_{20}$ hydrocarbyl group selected from one of alkyl, haloalkyl, alkylene, aryl, aralkyl, aralkylene, alkarylene, arylene, alkenyl or mixtures thereof; $R_1$ and $R_2$ are $C_1$ to $C_{22}$ hydrocarbyl group selected from one of alkyl, haloalkyl, alkylene, aryl, aralkyl, aralkylene, alkarylene, arylene, alkenyl or mixtures thereof; and wherein $R_1$ and $R_2$ may be the same or different;

the polyamine has the following general formula:

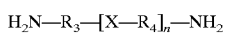

wherein $R_3$ and $R_4$ are $C_1$ to $C_6$ hydrocarbyl group selected from one of alkyl, haloalkyl, alkylene, aryl, aralkyl, aralkylene, alkarylene, arylene, alkenyl or mixtures thereof; X is selected from one or none of heteroatom or non-heteroatom, wherein the non-heteroatom comprises amine, thiol, or carboxyl, or $C_1$ to $C_6$ hydrocarbyl group selected from one of alkanol, alkyl, haloalkyl, alkylene, aryl, aralkyl, aralkylene, alkarylene, arylene, alkenyl or mixtures thereof; n is from 0 to 40; and $R_3$ and $R_4$ may be the same or different.

152. The process of claim 151, which further comprises preparing the polyamide in the presence of a hydrolytic enzyme.

153. The process of claim 151, wherein the polyamide has a molar ratio of reactant ester group of the diester:reactant primary amine group of the polyamine from about 0.8:1.1 to 1.1:0.8.

154. The process of claim 153, wherein diester comprises dialkyl malonate, dialkyl fumarate, dialkyl maleate, dialkyl adipate, dialkyl glutarate, dialkyl succinate, dialkyl oxalate, dialkyl phenylmalonate or mixtures thereof.

155. The process of claim 154, wherein the polyamine comprises diethylene triamine, triethylene-glycol diamine, ethylenediamine (EDA), bishexamethylenediamine (BHMT), hexamethylenediamine (HMDA), triethylenetetramine (TETA), tetraethylenepentamine (TEPA), dipropylenetriamine (DPTA), tripropylenetetramine (TPTA), tetrapropylenepentamine (TPPA), N-methyl-bis-(aminopropyl)amine (MBAPA), spermine, spermidine, 1-phenyl-2,4-pentane diamine, 2-phenyl-1,3-propanediamine, phenylene diamine or mixtures thereof.

156. The process of claim 155, wherein the polyamide comprises poly(diethylenetriamine adipamide), poly(diethylenetriamine glutaramide), poly(diethylenetriamine succinarnide), poly(diethylenetriamine malonamide), poly(diethylenetriamine oxalamide), poly(diethylenetriamine fumaramide), poly(diethylenetriamine phenylmalonamide), poly(diethylenetriamine maleamide), poly(triethylenetetraamine adipamide), poly(triethylenetetraamine glutaramide), poly(triethylenetetraamine succinamide), poly(triethylenetetraamine malonamide), poly (triethylenetetraamine oxalamide), poly(tetraethylenepentaamine adipamide), poly(tetraethylenepentaamine glutaramide), poly(tetraethylenepentaamine succinamide), poly(tetraethylenepentaamine malonamide), poly(tetraethylenepentaamine oxalamide), poly(bis(hexamethylene)triamine adipamide), poly(bis(hexamethylene)triamine glutaramide), poly(bis(hexamethylene)triamine succinamide), poly(bis(hexamethylene)triamine malonamide), poly(bis(hexamethylene)triamine oxalamide), poly(triethyleneamine malonamide), poly(tetraethyleneamine malonamide) or mixtures thereof.

157. The process of claim 153, wherein the polyamide has a molecular weight polydispersity from about 2.2 to 3.0.

158. A polyamide wherein the polyamide is prepared by the process of claim 151.

* * * * *